(12) United States Patent
Daske et al.

(10) Patent No.: US 11,793,959 B2
(45) Date of Patent: Oct. 24, 2023

(54) VENTILATOR WITH ADJUSTABLE USER INTERFACE

(71) Applicant: Drägerwerk AG & Co. KGaA, Lübeck (DE)

(72) Inventors: Jochen Daske, Lübeck (DE); Markus Hampe, Lübeck (DE); Robert Lischinski, Einhaus (DE); Andreas Nandzik, Berlin (DE); Eduard Engelsman, Lübeck (DE); Thomas Eckermann-Brahe, Wesel (DE); Christof Paul, Münster (DE); Volodymyr Savchuk, Stockelsdorf (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 223 days.

(21) Appl. No.: 16/981,150

(22) PCT Filed: Mar. 13, 2019

(86) PCT No.: PCT/EP2019/056253
§ 371 (c)(1),
(2) Date: Sep. 15, 2020

(87) PCT Pub. No.: WO2019/175221
PCT Pub. Date: Sep. 19, 2019

(65) Prior Publication Data
US 2021/0113794 A1   Apr. 22, 2021

(30) Foreign Application Priority Data

Mar. 16, 2018   (DE) .................... 10 2018 002 137.9
Jul. 4, 2018   (DE) .................... 10 2018 005 280.0

(51) Int. Cl.
*A61M 16/00* (2006.01)
*A61M 16/08* (2006.01)

(52) U.S. Cl.
CPC ...... *A61M 16/021* (2017.08); *A61M 16/0816* (2013.01); *A61M 2205/505* (2013.01); *A61M 2209/084* (2013.01)

(58) Field of Classification Search
CPC ................ A61M 16/00; A61M 16/202; A61M 2205/505; A61M 16/0816
See application file for complete search history.

(56) References Cited

U.S. PATENT DOCUMENTS 6,339,732 B1   1/2002   Phoon et al.
7,708,237 B2   5/2010   Mummert et al.
(Continued)

FOREIGN PATENT DOCUMENTS

CN   1483385 A   3/2004
CN   102004524 A   4/2011
(Continued)

*Primary Examiner* — Samchuan C Yao
*Assistant Examiner* — Tina Zhang
(74) *Attorney, Agent, or Firm* — McGlew and Tuttle, P.C.

(57) ABSTRACT

A ventilator (100), includes a basic unit (1) with a cover plate (10). Patient ports (4) are arranged at the basic unit (1) and a user interface (2) is arranged at the cover plate (10). The cover plate (10) can be arranged at the basic unit (1) at different angles in relation to a vertical axis.

20 Claims, 18 Drawing Sheets

(56) References Cited

U.S. PATENT DOCUMENTS

| | | | |
|---|---|---|---|
| 7,935,250 B2* | 5/2011 | Castellano | A61M 1/36 |
| | | | 210/143 |
| 8,011,362 B2 | 9/2011 | Adams | |
| 8,920,362 B2 | 12/2014 | Childers et al. | |
| 9,089,664 B2 | 7/2015 | Schermeier et al. | |
| 9,498,112 B1 | 11/2016 | Stewart et al. | |
| 10,299,759 B2* | 5/2019 | Messina | F16M 11/12 |
| 2002/0044059 A1 | 4/2002 | Reeder et al. | |
| 2004/0046487 A1 | 3/2004 | Olivera et al. | |
| 2004/0227045 A1* | 11/2004 | An | G06F 1/1643 |
| | | | 248/278.1 |
| 2005/0092873 A1 | 5/2005 | Lin | |
| 2008/0000477 A1 | 1/2008 | Huster et al. | |
| 2008/0123265 A1 | 5/2008 | Ohlinger | |
| 2008/0234577 A1* | 9/2008 | Murkowski | A61B 8/462 |
| | | | 361/825 |
| 2008/0274776 A1* | 11/2008 | Cho | H04M 1/0237 |
| | | | 455/575.4 |
| 2009/0284108 A1 | 11/2009 | Castellano et al. | |
| 2011/0053651 A1 | 3/2011 | Miyashita et al. | |
| 2011/0203592 A1* | 8/2011 | Adams | A61M 16/06 |
| | | | 128/205.25 |
| 2012/0175474 A1* | 7/2012 | Barnard | F16M 11/14 |
| | | | 248/122.1 |
| 2012/0289765 A1 | 11/2012 | Kaushansky et al. | |
| 2015/0122259 A1* | 5/2015 | Fox | A61M 16/0096 |
| | | | 128/204.19 |
| 2015/0202105 A1 | 7/2015 | Drapes et al. | |
| 2015/0202362 A1 | 7/2015 | Wolff et al. | |
| 2017/0304570 A1* | 10/2017 | Landis | A61M 16/0051 |

FOREIGN PATENT DOCUMENTS

| | | |
|---|---|---|
| CN | 202188013 U | 4/2012 |
| CN | 103619370 A | 3/2014 |
| CN | 104582754 A | 4/2015 |
| CN | 104644115 A | 5/2015 |
| CN | 204314992 U | 5/2015 |
| CN | 105411557 A | 3/2016 |
| CN | 105667413 A | 6/2016 |
| CN | 106774693 A | 5/2017 |
| CN | 207049177 U | 2/2018 |
| EP | 1396235 A1 | 3/2004 |
| JP | 2017006476 A | 1/2017 |
| WO | 2008010004 A1 | 1/2008 |
| WO | 2012158560 A2 | 11/2012 |
| WO | 2016043644 A1 | 3/2016 |
| WO | WO-2016043644 A1 * 3/2016 ........... B23B 51/108 |

* cited by examiner

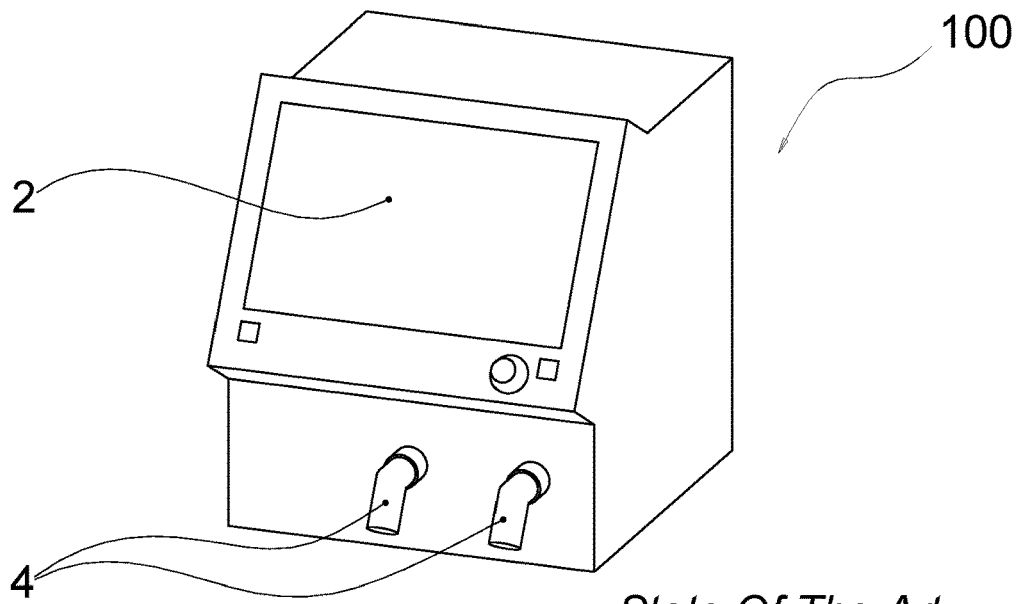
*Fig. 2*  *State Of The Art*
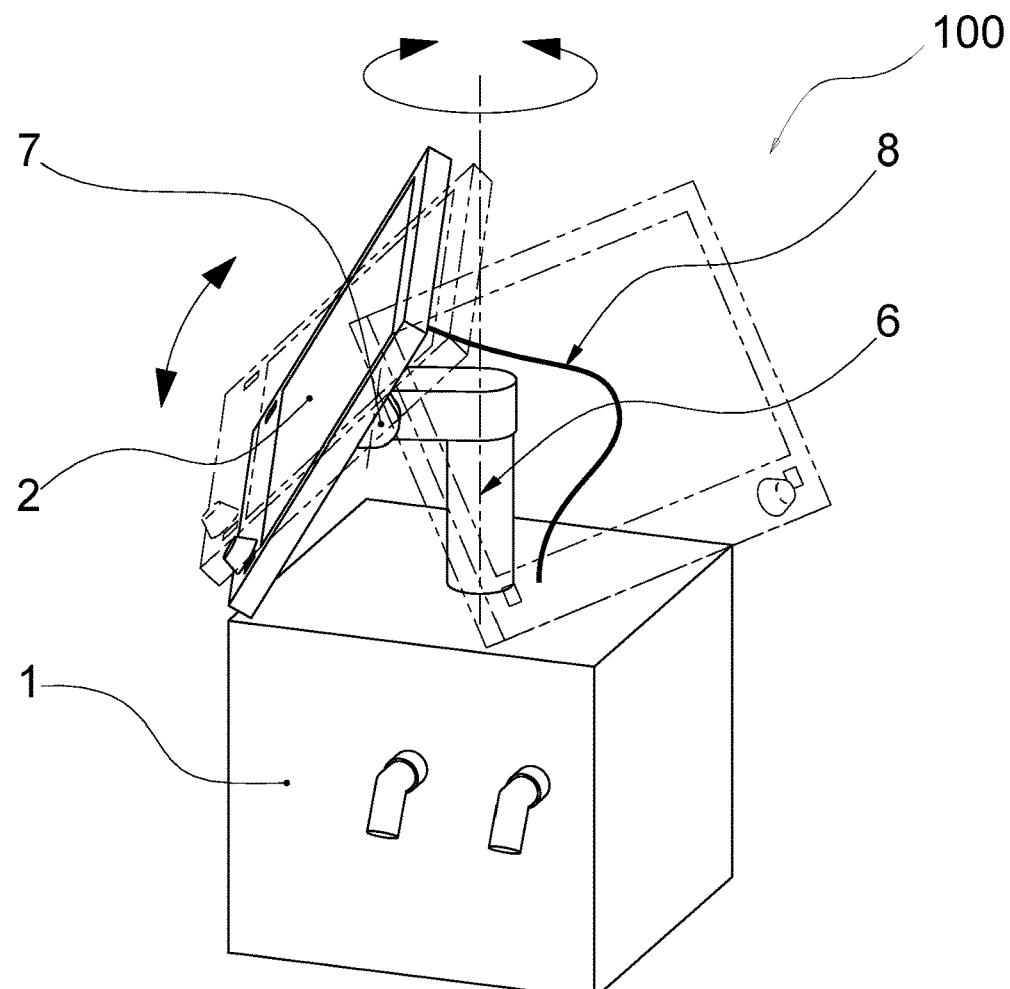
*State Of The Art*  *Fig. 3*

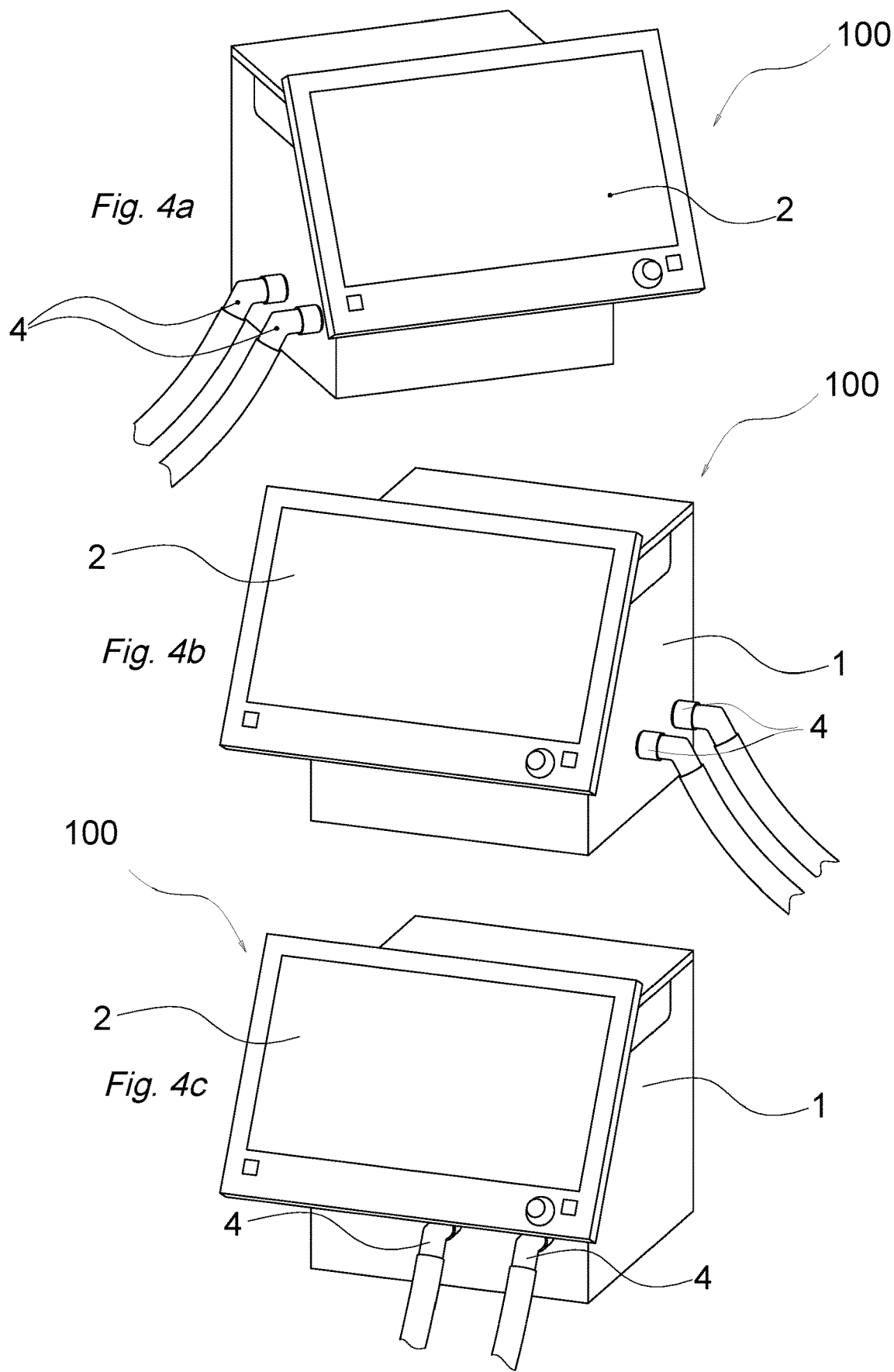

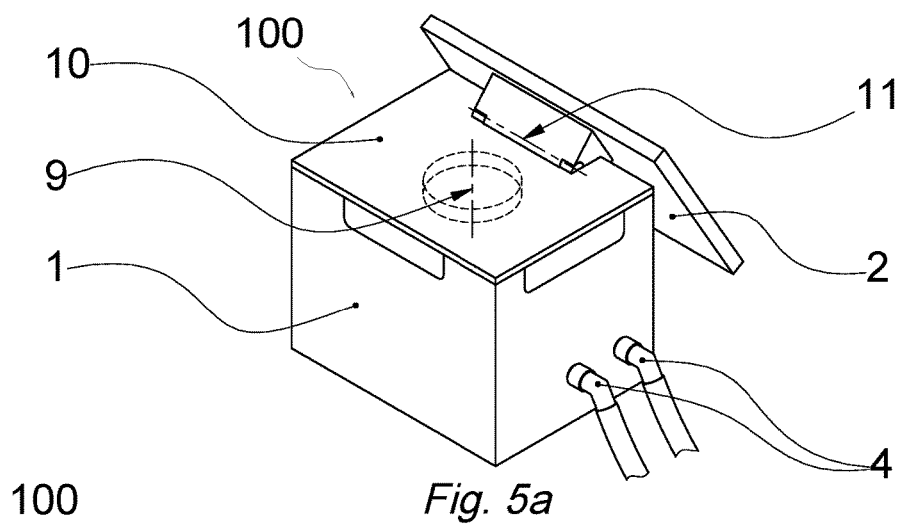
Fig. 5a
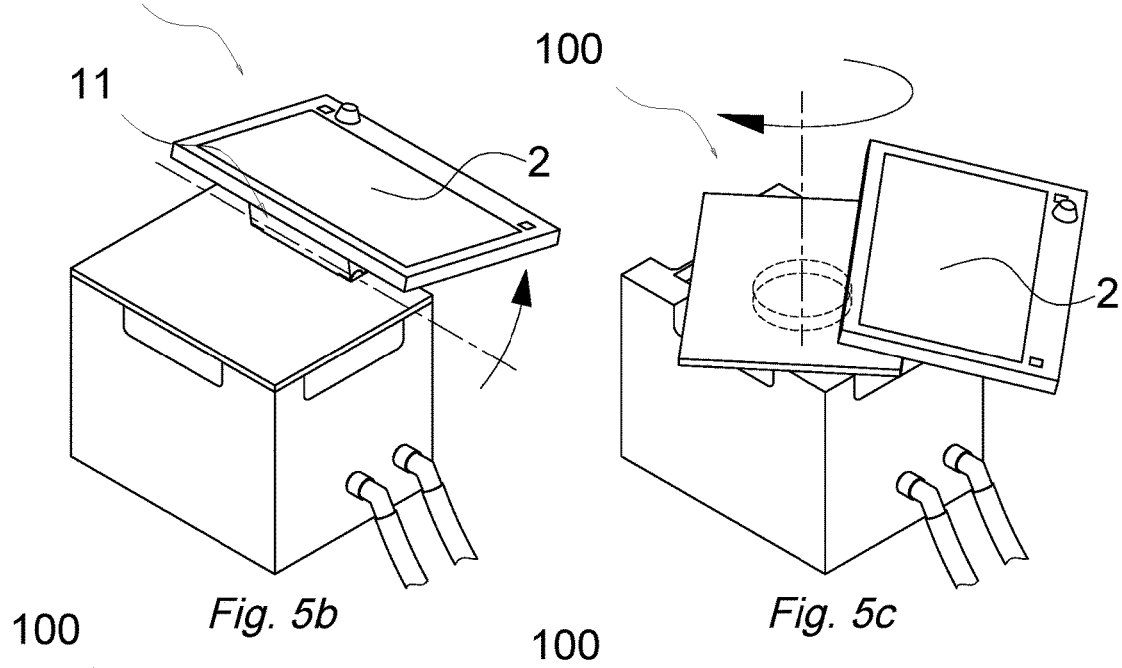
Fig. 5b
Fig. 5c
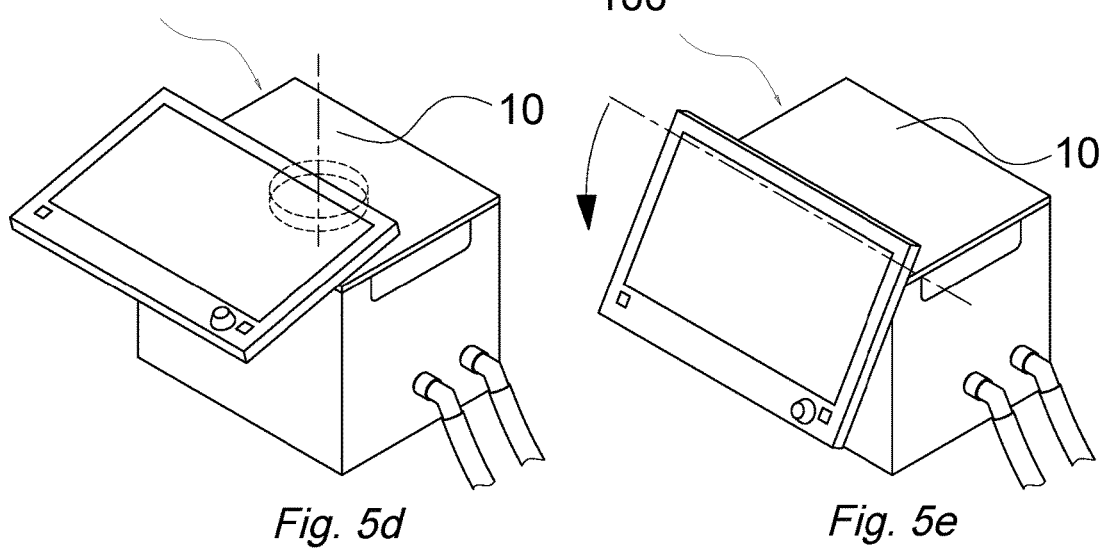
Fig. 5d
Fig. 5e

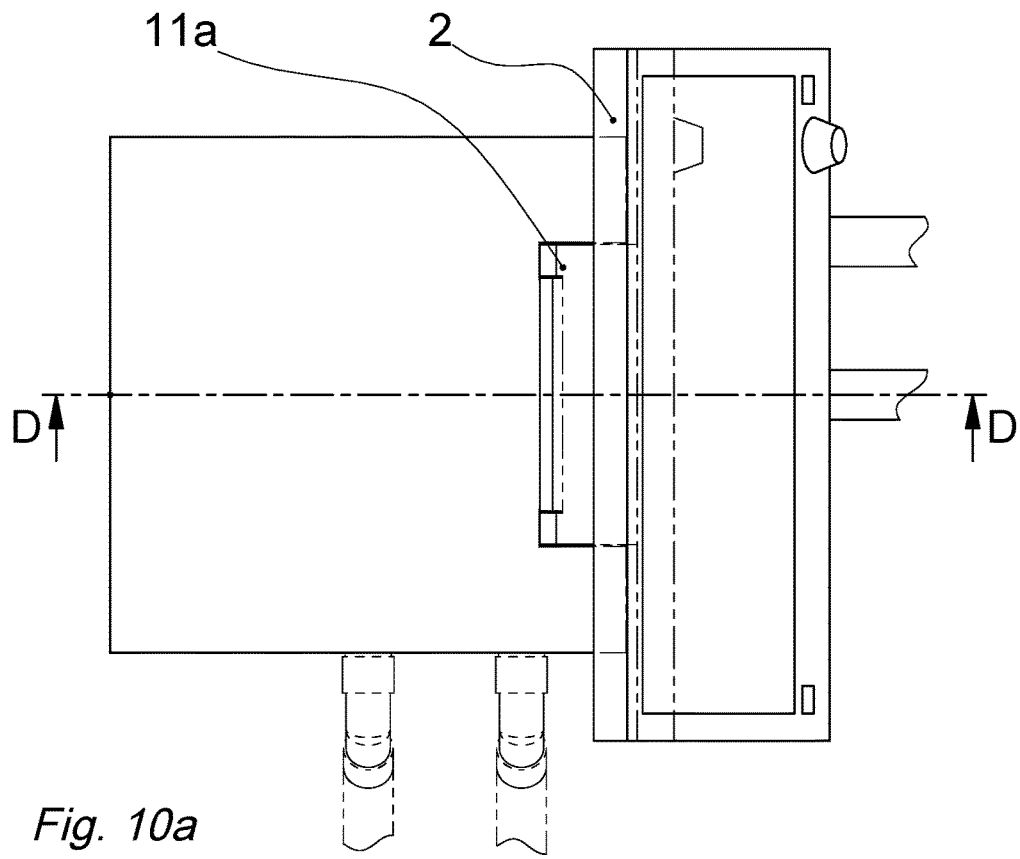
*Fig. 10a*
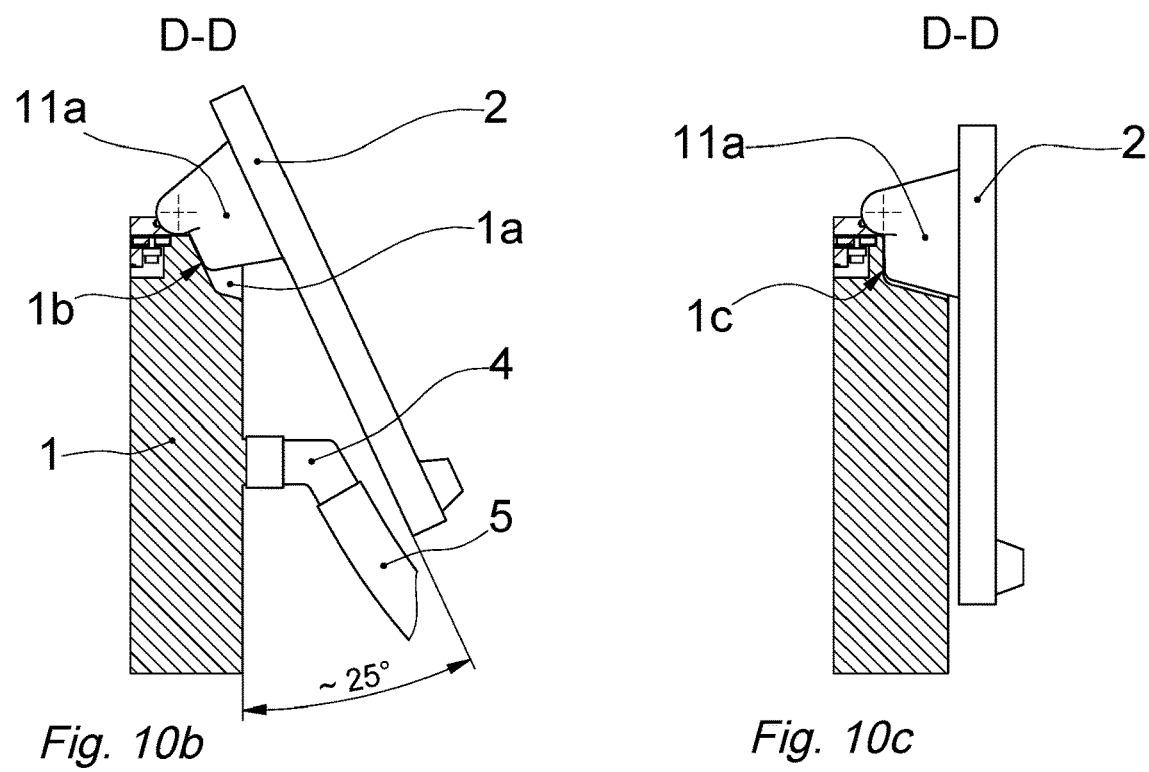
*Fig. 10b*  *Fig. 10c*

VENTILATOR WITH ADJUSTABLE USER INTERFACE

CROSS REFERENCE TO RELATED APPLICATIONS

This application is a United States National Phase Application of International Application PCT/EP2019/056253, filed Mar. 13, 2019, and claims the benefit of priority under 35 U.S.C. § 119 of German Applications 10 2018 002 137.9, filed Mar. 16, 2018 and 10 2018 005 280.0, filed Jul. 4, 2018, the entire contents of which are incorporated herein by reference.

TECHNICAL FIELD

The present invention pertains to a ventilator for clinical use, comprising a basic unit, a corresponding user interface and an optional trolley, on which the ventilator is arranged.

TECHNICAL BACKGROUND

A ventilator usually has a cuboid housing for receiving pneumatic and electronic components and has interfaces for gas inlets and gas outlets as well as additional, mainly electrical interfaces. The arrangement of the patient connections for the ventilation tubes which lead to the patient and return from the patient to the device are of particular significance in this connection.

Modern ventilators are controlled via a large-surface user interface with a touchscreen, which displays important ventilation parameters, for example, set and measured therapy values as well as pressure and volume curves, and makes different interactions available to the user. Additional hardware components, such as a rotary knob and/or buttons, are often arranged under or next to the touchscreen for special functions.

Ventilators of different performance classes frequently differ in terms of the configuration of the housing in the manner in which the user interface is connected to the basic unit.

Devices of the lower performance classes integrate the often comparatively small user interface into the basic unit, frequently at an angle that is selected according to ergonomic criteria but is not changeable. The user interface and the patient connections are usually oriented in the same direction in such devices. Advantages of such an embodiment are the smaller dimensions of the device and the cost-effective configuration of the housing.

By contrast, devices of higher performance classes frequently have a user interface, which is separated from the basic unit and which can be positioned freely with respect to the basic unit in two degrees of freedom, for example, by means of a vertical axis and a swivel joint. The user interface is connected to the basic unit in this case by an exposed cable, especially a system cable. It is often possible in the case of such devices to remove the user interface and to arrange it at another location in the vicinity of the patient, for example, by means of a rail claw on a standard rail. The advantage of such a flexible arrangement is that both patient connections and a user interface can be positioned ergonomically optimally, so that, for example, patient connections can be positioned in the direction of the patient and the user interface in the direction of the physician.

The state of the art in the field of compact ventilators is represented essentially by devices with a housing architecture as it is shown, for example, in FIG. 2. Such a device is, for example, the Dräger Savina 300® of Drägerwerk AG & Co. KGaA. Other devices have, by contrast, a semi-integrated user interface, whose slope can be set by means of a swivel joint. An example of a device having such a configuration is the ventilator SV 300 of the firm of Mindray.

The above-described technical solutions are characterized in that the relative position between the user interface and the patient connections cannot be changed. If the patient connections are oriented in the direction of the patient, which is desirable in view to reducing the dead space and hence to ensure an improved ventilation performance, the display is not frequently oriented optimally towards the patient. In addition, an ergonomically optimized adjustment of the slope of the user interface is not possible at least in the case of the devices of the above-described configuration, which lack slope adjustment. Furthermore, it is often problematic that this inevitably leads to an increase in the overall height of the entire device due to the use of a large-surface touchscreen, which is required for modern Graphical User Interfaces, because the user interface is arranged above the patient connections.

In addition to the above-described ventilators, devices of higher performance classes are known, which have a separate operating part. The housing architecture of these devices is shown in FIG. 3. An example of such a device is represented by Dräger Evita® Infinity® 500 of Drägerwerk AG & Co. KGaA. Further, the device Servo-i® of the firm of Maquet is known, which makes it additionally possible to reconfigure the patient connections from one side to the other side by turning the basic unit on the trolley by 180°.

The above-described technical solutions are characterized by a tall configuration due to the arrangement of the user interface above the basic unit, so that much space is needed for installation in the vertical direction. Therefore, either a composite system, which also includes the trolley as a support structure, or a separate mounting of the basic unit and the user interface at stationary holding systems is common in these devices. The design effort is therefore comparatively great, and the axle, the swivel joint as well as cables and system cables are exposed and form additional external surfaces, which must also be disinfected in connection with the preparation of the device for use.

SUMMARY

Based on the technical solutions known from the state of the art, a basic object of the present invention is to provide a ventilator, which combines in itself the advantageous features of a compact device, as it is shown in FIG. 2, with those of a comparatively flexible device of a higher performance class, as it can be seen in FIG. 3. In particular, a device shall be provided that can be used in a flexible manner and at the same time has a comparatively simple configuration and an easy-to-operate mechanism for moving a user interface, e.g. a display and/or an operating unit. The user interface of the device shall preferably be able to be repositioned into different positions in a simple and reliable manner, so that the patient connections for the necessary ventilation tubes are arranged on different sides relative to the display and/or to the operating unit. Further, the ventilator to be proposed shall provide a simple configuration with the smallest possible external dimensions, but it shall nevertheless be able to be equipped with the largest possible operating part. In particular, a device shall be provided in which an arrangement in which the patient connections point to the left with respect to the operating part and/or the display can be reconfigured without much effort into an opposite arrangement in which the patient connections point to the right. The optional possibility of setting a third configuration in which the patient connections point forward would, furthermore, be advantageous.

The ventilator according to the present invention has a basic unit with a cover plate, patient connections arranged at the basic unit and a user interface arranged at the cover late. According to the present invention the cover plate can be arranged at the basic unit at different angles with respect to a vertical axis. According to the present invention the ventilator may also be configured as an integral part of an anesthesia device for anesthetizing a patient.

Preferably the basic unit of the ventilator has a housing which shields an interior from a surrounding area. In addition, the basic unit is preferably configured as a core device of the ventilator and hence for generating a breathing air stream. A connection device for a power supply is preferably arranged at the basic unit. Further, the basic unit is electrically coupled to the user interface via an electrical connection, so that technical functions of the basic unit can be controlled by means of the user interface. The patient connections are preferably arranged laterally at the basic unit. Provisions may also be made for the patient connections to be arranged at an underside of the basic unit. As an alternative, the patient connections may be distributed over a plurality of sides of the basic unit.

The cover plate preferably has a shape that corresponds to the shape of the layout of the basic unit, so that the cover plate is flush with side walls of the basic unit when being arranged accordingly. The cover plate is rotatable about the vertical axis by different angles with respect to the basic unit.

The user interface is preferably configured as a display and/or operating part. A preferred user interface is configured as a touchscreen monitor. In addition or as an alternative, the user interface may have mechanical buttons and/or shaft encoders. In addition, the user interface is arranged adjacent to at least one section of the cover plate. The user interface can thus be moved relative to the basic unit with respect to the vertical axis into another position by a relative adjustment of an angle of the cover plate to the basic unit with respect to the vertical axis. The user interface can preferably be arranged at the cover plate such that this user interface is arranged obliquely with respect to the cover plate. A plane containing the cover plate preferably intersects the user interface along a straight line. It is especially preferred that the user interface is held at an edge area of the cover plate. Preferably an edge area of the user interface is also held at the cover plate.

The ventilator according to the present invention has the advantage over conventional ventilators that thanks to an especially compact overall size it is achieved that the user interface can be arranged in different positions with respect to the basic unit. In particular the user interface can be arranged with respect to a chassis of the ventilator and/or to a functional unit of the ventilator having a ventilating unit and having the necessary pneumatic components. The patient connections for the ventilation tubes can be arranged in this manner on different sides of the operating part, monitor and/or display depending on the arrangement of the operating part, of the monitor and/or of the display. Variable positions of the user interface with respect to the patient connections can thus be achieved. The ventilator according to the present invention can thus be configured for different applications in an especially advantageous manner.

The cover plate is preferably held rotatable about a vertical axis by means of a rotating mechanism. For this reason, the cover plate is preferably arranged such that a small gap is formed at the basic unit in order to avoid grazing between the cover plate and the basic unit. The cover plate is arranged as close to the basic unit as possible in order to ensure an especially compact overall size of the ventilator. The rotating mechanism has, for example, a rolling bearing or a plain bearing or the like. A rotating mechanism has the advantage that the arrangement of the cover plate with respect to the basic unit at a different angle with respect to the vertical axis is improved, because the relative movement of the cover plate with respect to the basic unit is guided by means of the rotating mechanism and it can thus take place as a rotation.

Provisions may be made according to the present invention for the ventilator, especially the rotating mechanism, to have a locking mechanism which noticeably impedes a relative rotation of the cover plate with respect to the basic unit at predefined distances, for example, at distances of 90° or 180°. It is possible, for example, to provide locking positions at 0°, 90°, 180° and 270°. The locking positions preferably correspond to use positions of the cover plate. Such locking positions have the advantage that a defined relative orientation of the cover plate with respect to the basic unit is facilitated.

The ventilator preferably has rotation stop elements for limiting a rotation of the cover plate about the vertical axis relative to the basic unit. The rotation stop elements may be formed, for example, at the rotating mechanism. As an alternative or in addition, the rotation stop elements may be arranged at the basic unit as well as at the cover plate. The rotation stop elements are preferably configured and arranged such that a relative rotation of the cover plate with respect to the basic unit by about 360° and especially by 180° is possible. An uncontrolled twisting of cables, which connect the basic unit to the operating part, is advantageously prevented with simple means by a limitation of the rotary motion of the cover plate.

According to a preferred variant of the present invention, provisions may be made in the ventilator for the cover plate to have a layout configured rotationally symmetrically by 180° or by 90°. A rotationally symmetrically configured layout is also defined within the framework of the present invention as an essentially rotationally symmetrically configured layout, so that the cover plate may have, for example, a local recess or clearance and/or shape allowance, by which a pure rotational symmetry would not be achieved. A cover plate configured with a rotational symmetry by 180° has, for example, a rectangular or oval base. A cover plate configured with a rotational symmetry by 90° has, for example, a square base or a round base. It is preferred in this connection that the cover plate is arranged flush or at least symmetrically to side walls of the basic unit. Such an especially rectangular or square cover plate has the advantage that such an orientation of the cover plate in the correct position with respect to the basic unit can easily be achieved. A predefined relative position of the user interface and of the patient connections can thus be set with simple means by means of the ventilator according to the present invention.

The user interface is preferably also held pivotably about a horizontal pivot axis at the cover plate by means of a swivel joint. The swivel joint may be configured, for example, as a hinge, as a ball joint or the like. The user interface is mounted in a rotatingly movable manner at an edge area of the cover plate. The swivel joint is or can preferably be arranged at an edge area of the user interface and/or at an edge area of the cover plate. A relative angle of the user interface with respect to the cover plate and hence also with respect to the basic unit can be set in this manner. A swivel joint has the advantage that orientation of the user interface to a user of the ventilator, for example, a physician, can be improved with simple means and in a cost-effective manner.

Further, it is preferred that the ventilator has a locking device for holding the user interface in a locked position relative to the cover plate. Especially preferably the locking device is arranged or formed at the swivel joint. The locking device is preferably configured to hold the user interface in a plurality of locking positions. A set relative angle of the user interface with respect to the cover plate as well as to the basic unit can be temporarily fixed in this manner. An unintended change of the angle can thus be avoided with simple means as well as in a cost-effective manner.

According to a preferred embodiment of the present invention, the swivel joint is configured to pivot the user interface into an at least approximately horizontal position. A horizontal position means within the framework of the present invention that the user interface is arranged parallel or at least essentially parallel to the cover plate. This has especially the advantage that a collision of the user interface with the basic unit during the relative rotation of the cover plate with respect to the basic unit can be better avoided in this manner. In addition, such a pivotability is advantageous when the swivel joint is or can be arranged at an edge area of the user interface and/or at an edge area of the basic unit. The user interface can be pivoted in this case, for example, such that it covers the cover plate or is arranged within a layout shape of the cover plate. Such a pivotability has the advantage that outside dimensions of the ventilator can thus be reduced.

The user interface can preferably be pivoted into a blocking position by means of the swivel joint when the cover plate is in a use position, in which case a relative rotation of the cover plate with respect to the basic unit is blocked by the blocking position of the user interface. The user interface can then be pivoted into a releasing position, in which a relative rotation of the cover plate with respect to the basic unit is released. A blocking position is set preferably such that the user interface is pivoted in an operating position. The operating position may extend, for example, over a pivoting range, especially between a vertical orientation of the user interface to a transition orientation of the user interface. The releasing position is preferably defined such that the user interface is pivoted between the transition position and the horizontal orientation. The transition orientation preferably deviates from the horizontal orientation by between 0° and 20°. The blocking effect in the blocking position may be achieved, for example, by the user interface, which comes to engage with the basic unit, especially in a positive-locking manner. Pivotability into a blocking position has the advantage that an unintended rotation of the cover plate from a use position or a locking position can be avoided with simple means as well as in a cost-effective manner.

It is preferred according to the present invention that the swivel joint is configured to block the cover plate in a use position when the user interface is in the blocking position. The swivel joint is preferably configured to block the cover plate in a plurality of different intended use positions when the user interface is in the blocking position. The swivel joint accordingly has a configuration that achieves the blocking effect when the swivel joint is pivoted into the blocking position. The swivel joint is preferably configured to engage, especially in a positive-locking manner, with the basic unit in the blocking position. Such a configuration of the swivel joint has the advantage that damage to the user interface can be avoided with simple means as well as in a cost-effective manner.

The basic unit is preferably arranged on a trolley of the ventilator. Within the framework of the present invention a trolley is a device that facilitates a movement of the ventilator on a floor surface. Preferably the trolley has wheels and/or rollers for this purpose. The trolley preferably also has a stand device in order to make it possible to arrange the basic unit at a working level, for example, 100 cm. Preferably the stand device has a telescoping configuration in order to make it possible to arrange the basic unit at different working levels. In addition, provisions may be made in a trolley for the trolley to have holding devices for gas cylinders, humidifiers or the like. A trolley has the advantage that positioning of the ventilator, especially of the user interface as well as of the patient connections, can be improved with simple means as well as in a cost-effective manner and a ventilator can be moved in a simple manner as needed from a storage room to the patient and/or from patient to patient. In addition, a trolley makes it possible to transport a patient requiring ventilation, for example, to a diagnostic facility by jointly moving the patient and the trolley with the ventilator.

Preferably the basic unit is detachably held at the trolley via a support plate of the trolley. For this purpose, the support plate has mounts which can be connected with counter-mounts of the basic unit. The mounts may be configured, for example, as recesses and the counter-mounts as pins. The support plate preferably has a rotationally symmetrical configuration by 180° or 90°. In addition, a blocking device is provided for blocking the basic unit at the support plate in order to prevent an unintended separation of the basic unit from the support plate, for example, because of an unintended tilting of the trolley. A support plate has the advantage that a defined position of the basic unit with respect to the trolley can easily be achieved. In addition, the basic unit can easily be fixed at the support plate in order to avoid an unintended separation of the basic unit from the trolley.

It is preferred according to the present invention that the basic unit and the support plate are configured such that the basic unit can be arranged as well as fixed on the support plate in two positions differing from one another by 180° or in at least three, preferably four different positions differing from one another by 90°. Two configurations of the ventilator, which are preferably optimized for arrangement on the left and on the right next to a hospital bed, can be achieved in this manner. A ventilator configured for being positioned on the left next to a hospital bed can thus easily be reconfigured for use on the right next to a hospital bed, namely, by a rotation about 180° relative to the support plate. The entire basic unit can preferably be arranged and fixed on the support plate in three or four positions differing from each other by 90°. In this manner it is possible to obtain three or four configurations of the ventilator, which configurations are preferably optimized for arrangement on the left or on the right next to, behind or in front of a hospital bed. A ventilator configured for being arranged on the left next to a hospital bed can thus easily be reconfigured for use in front of or behind a hospital bed, namely, by rotation about 90° relative to the support plate. A possibility for an easy reconfiguration of the ventilator is improved in this manner with simple means as well as in a cost-effective manner.

The user interface is preferably arranged at the cover plate such that it can linearly be shifted, especially arranged linearly slidable at the swivel joint. The user interface can preferably be shifted linearly at right angles to and/or parallel to the pivot axis. The user interface is preferably arranged slidable at the swivel joint such that the swivel joint is arranged in a first position at an edge area, especially in a lower edge area, of the user interface. Furthermore, the user interface is preferably arranged slidable at the swivel joint such that the swivel joint is arranged in a second position at a central area or upper edge area of the user interface. This feature can be achieved, for example, by means of a linear guide. Preferably the linear guide has a locking device for avoiding an unintended linear adjustment of the user interface. Such a displaceability has the advantage that the user-friendliness of the ventilator can be improved hereby. For example, an orientation of the user interface with respect to a user of the ventilator can thus be improved. Furthermore, the storability of the ventilator can be improved hereby.

According to a preferred embodiment of the present invention, provisions may be made in a ventilator for at least one patient connection to be arranged pivotably at the basic unit. Pivotable patient connections have the advantage that the orientation of ventilation tubes with respect to the patient can be improved, such that an unintended mechanical load or even kinking of the ventilation tubes can be avoided.

The rotating mechanism preferably has a central passage, through which cables can or are passed for the electrical coupling of the user interface with the basic unit. A central passage has the advantage that movement of the cables during the rotation of the cover plate relative to the basic unit is minimized. Damage to the cables can thus be avoided in a cost-effective manner as well as with simple means.

Further measures improving the present invention appear from the following description in connection with some exemplary embodiments of the present invention, which are shown in the figures. All the features and/or advantages, including design details and arrangements in space, which appear from the claims, from the description or from the drawings, may be essential for the present invention both in themselves as well as in the various combinations. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 2 is a perspective view of a compact ventilator according to the state of the art;

FIG. 3 is a perspective view of a flexibly configurable ventilator according to the state of the art;

FIG. 4a is a perspective view of one of different configurations of a preferred embodiment of a ventilator according to the present invention;

FIG. 4b is a perspective view of another of different configurations of a preferred embodiment of a ventilator according to the present invention;

FIG. 4c is a perspective view of another of different configurations of a preferred embodiment of a ventilator according to the present invention;

FIG. 5a-5e are perspective views of two configurations of a preferred embodiment of a ventilator according to the present invention with intermediate steps, which show the reconfiguration process;

FIG. 10a is a top view of a preferred embodiment of a ventilator according to the present invention with swivel joint in the blocking position;

FIG. 10b is a sectional view of a preferred embodiment of a ventilator of FIG. 10a according to the present invention with swivel joint in the blocking position;

FIG. 10c is another sectional view of a preferred embodiment of a ventilator of FIG. 10a according to the present invention with swivel joint in the blocking position;

DESCRIPTION OF PREFERRED EMBODIMENTS

Figure 1:
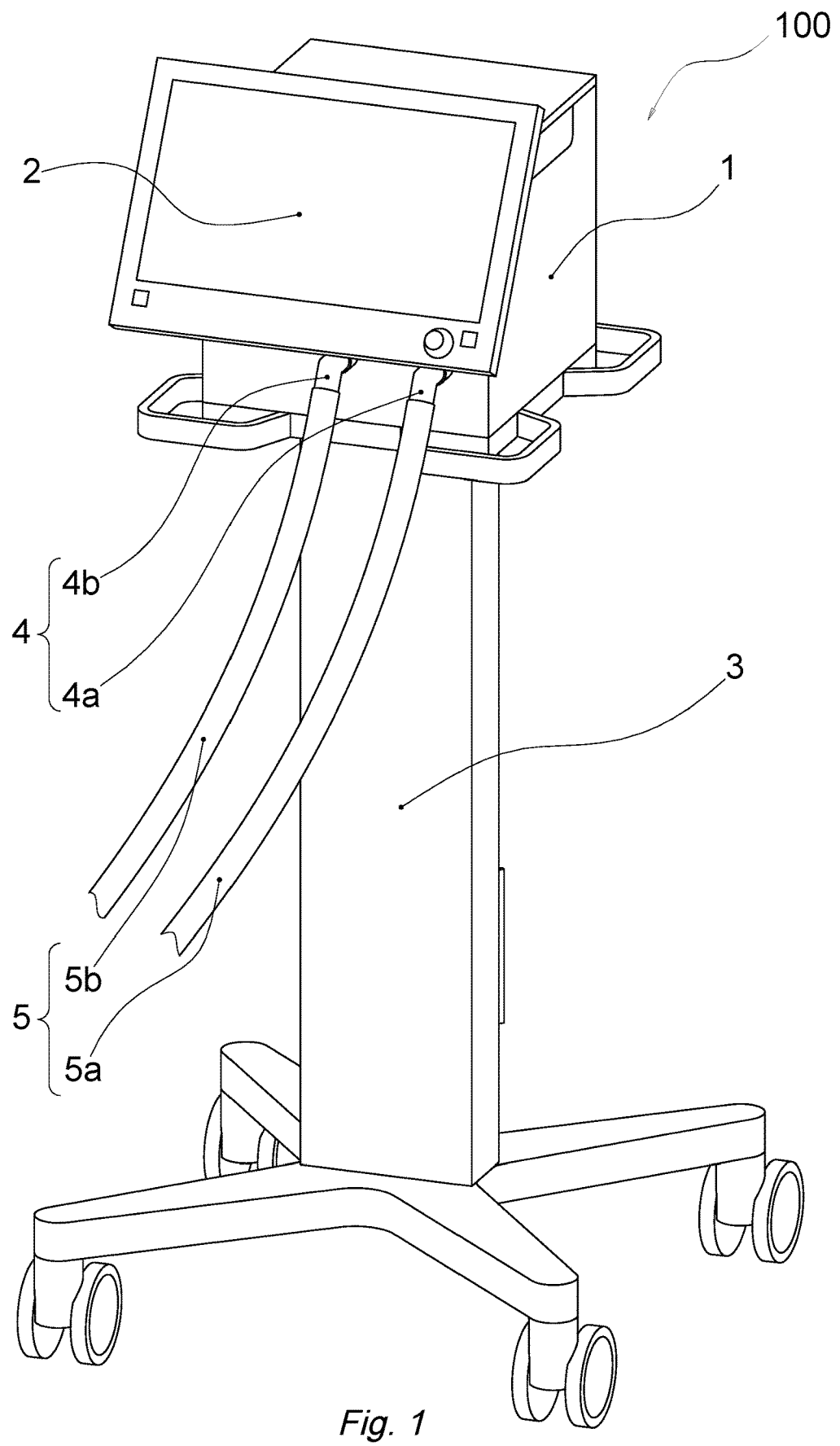
FIG. 1 is a perspective view of a preferred embodiment of a ventilator according to the present invention.
Figure 6A:
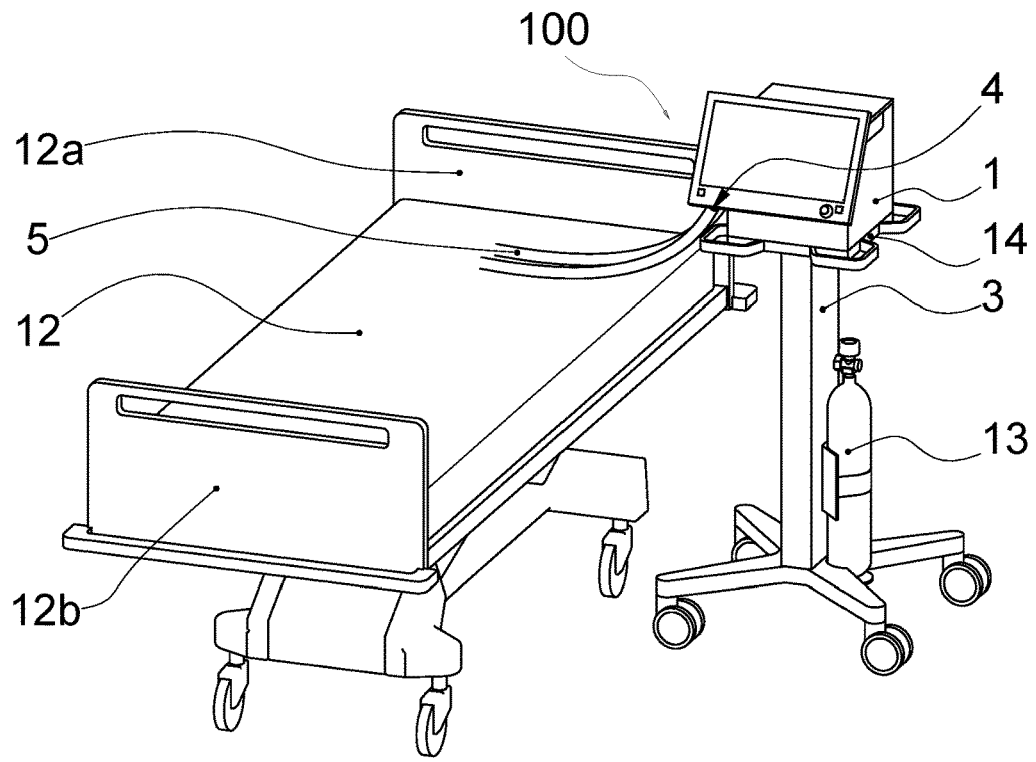
FIGS. 6a-6h are perspective views of different arrangements of a preferred embodiment of a ventilator according to the present invention at a hospital bed.
Figure 6B:
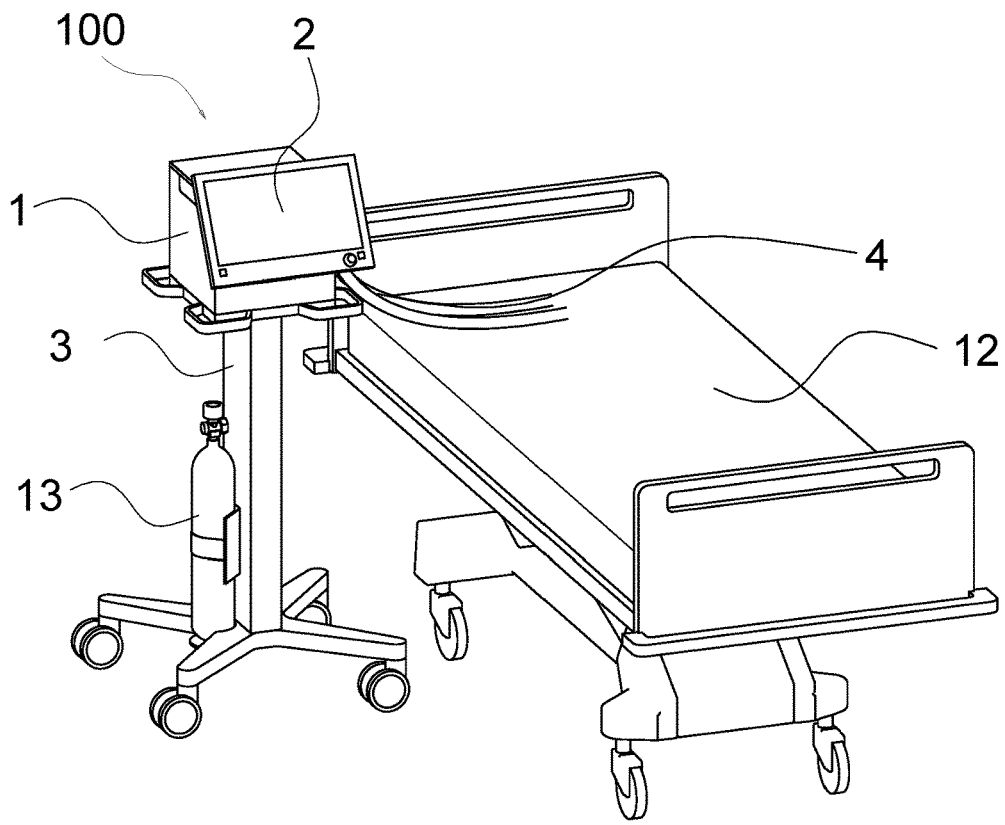

Referring to the drawings, FIG. 1 schematically shows a preferred embodiment of a ventilator 100 according to the present invention in a perspective view. According to this embodiment, the ventilator 100 has a trolley 3, to which a basic unit 1 of the ventilator 100 is connected. When the device is positioned, as is shown in FIG. 1, on a trolley 3, mainly two arrangements occur in hospitals: The device stands next to the hospital bed 12 on the right side (FIGS. 6a, c, e) or next to the hospital bed 12 on the left side (FIGS. 6b, d, f). It is advantageous in both arrangements if the patient connections (patient ports) 4 are oriented towards the patient in order to keep the lengths of the ventilation tubes 5 as short as possible, while the user interface should be oriented towards the foot end of the hospital bed 12 in order to be able to be clearly seen and operated by the patient.

The ventilator 100 according to the present invention has, according to the special embodiment shown in FIGS. 5a-e, a basic unit 1 with laterally arranged patient connections 4 and with a cover plate 10 mounted thereon by means of a vertical rotating mechanism 9. A user interface 2 is connected, in turn, to the cover plate 10 via a swivel joint 11. To transfer the ventilator 100 from the state shown in FIG. 5*a* into the state according to FIG. 5*e*, the user interface 2 is pivoted first into an at least approximately horizontal position upward by actuating the swivel joint 11, so that the user interface 2 will then be able to be rotated by 180° to the opposite side (FIGS. 5*c-d*) by means of the rotatably mounted cover plate 10, without colliding with the basic unit 1. The user interface 2 is then pivoted down again into the desired angular position (FIG. 5*e*) on this side of the basic unit 1 by means of the swivel joint 11.

A reconfiguration of the ventilator 100, as it is described above, preferably provides for a 180° rotationally symmetrical, especially preferably rectangular layout of the basic unit 1 and of the cover plate 10, in order for the cover plate 10 to be able to assume a congruent layout with respect to the basic unit 1 in both end positions.

An expanded functionality, which functions, in principle, in exactly the same manner, can be obtained according to another embodiment by the cover plate 10 being able to be rotated in increments of 90° with respect to the basic unit 1 (as is shown in FIGS. 4*a-c*). A position of the user interface 2 in the same orientation as that of the patient connections 4 is also possible as a result, and, in principle, even a fourth position, in which the user interface 2 located opposite the patient connections 4, is possible as well. The layout of the basic unit 1 and of the cover plate 10 must be rotationally symmetrical by 90°, preferably square, for this expanded functionality.

The general configuration of the mechanism described is the same as in the case of a ventilator 100 according to FIG. 3. The user interface 2 according to the present invention is likewise connected to the basic unit 1 by means of a vertical rotating mechanism 9 and, adjoining this, by a horizontal swivel joint 11.

The decisive difference is the integration of the vertical rotating mechanism 9 into a cover plate 10 that is flush with the basic unit 1 and the user interface 2, which is arranged in front of the basic unit 1 in as low a position as possible rather than above the basic unit 1. As a result, the overall arrangement leads to a compact ventilator 100 with a low overall height despite a large user interface 2. A cable 8, especially a system cable, for connecting the user interface 2 to the basic unit 1 is advantageously routed on the inside, which is better from the viewpoint of hygiene and reinforces the impression of a compact ventilator 100.

According to special variants, the user interface 2 can be positioned only in 180° increments (device according to FIGS. 5*a-e*) and 90° increments (device according to FIGS. 4*a-c*) with respect to the basic unit 1. It is, however, also conceivable, in general, that a free rotation about the vertical axis is made possible, as it is also possible with the ventilator 100 according to FIG. 3.

According to the embodiment shown in FIGS. 5*a-e*, the ventilator 100 may be configured for both a configuration on the right of the hospital bed 12 and a configuration on the left of the hospital bed 12, in which case there are different possibilities for the orientation of the patient connections 4 towards the patient. The trolley 3 as a whole may be turned towards the patient, as it is shown in FIG. 6*a* and in FIG. 6*b*. This is the simplest solution in terms of handling, but it does have the drawback that accessories arranged at the trolley 3, for example, a humidifier, an articulated arm or a gas cylinder 13, cannot be arranged optimally in both positions and may have to be rearranged. A gas cylinder 13 with a holder is shown as an example.

It is advantageous, by contrast, if the basic unit 1 can likewise be repositioned or reconfigured on the trolley 3, so that the trolley 3 maintains the same position (FIG. 6*c* and FIG. 6*d*) in both arrangements. According to a special variant of the present invention, a connection that can be detached in a simple manner is provided between a support plate 14 of the trolley 3 and the basic unit 1, which connection has, in turn, a 180° rotation symmetry. For the repositioning, the basic unit 1 is preferably unlocked, raised and placed back again, rotated by 180°, on the support plate 14 of the trolley 3. The subsequent blocking may take place automatically. A rotating device, not shown, by means of which the basic unit 1 can be turned on the trolley 3 after actuating an unblocking device until it snaps in again automatically in the next end position provided, i.e., after 180°, is also more user-friendly as an alternative, albeit it has a more complicated configuration.

Figure 6C:
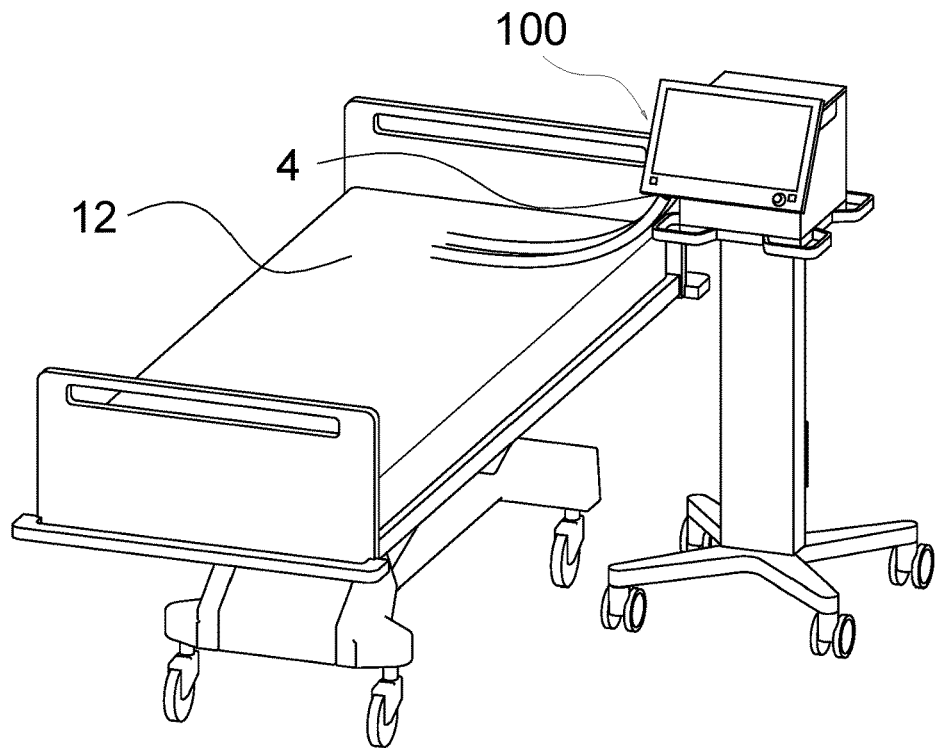
Figure 6D:
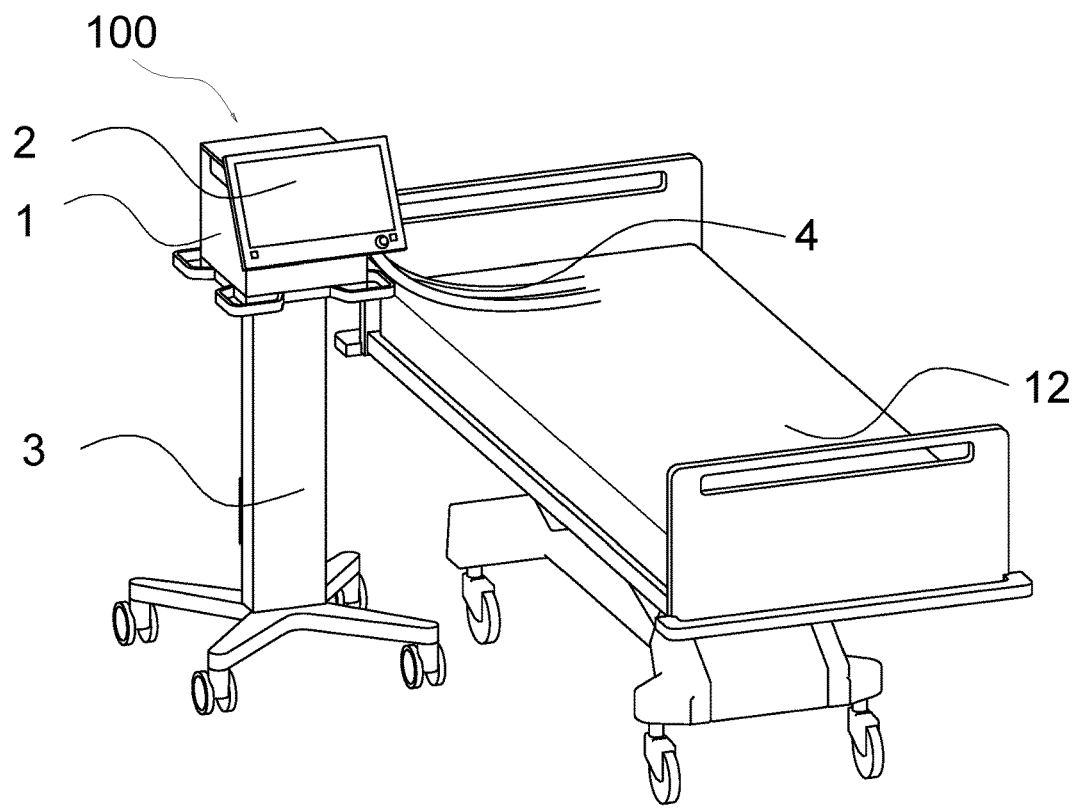
Figure 6E:
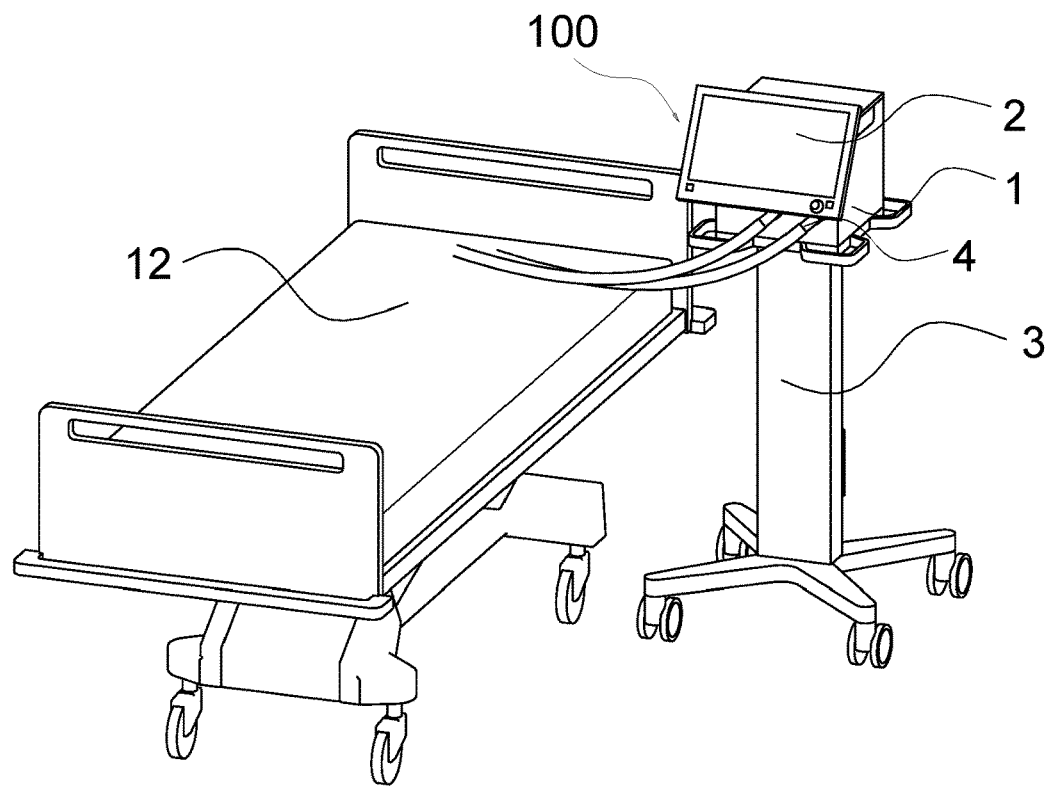
Figure 6F:
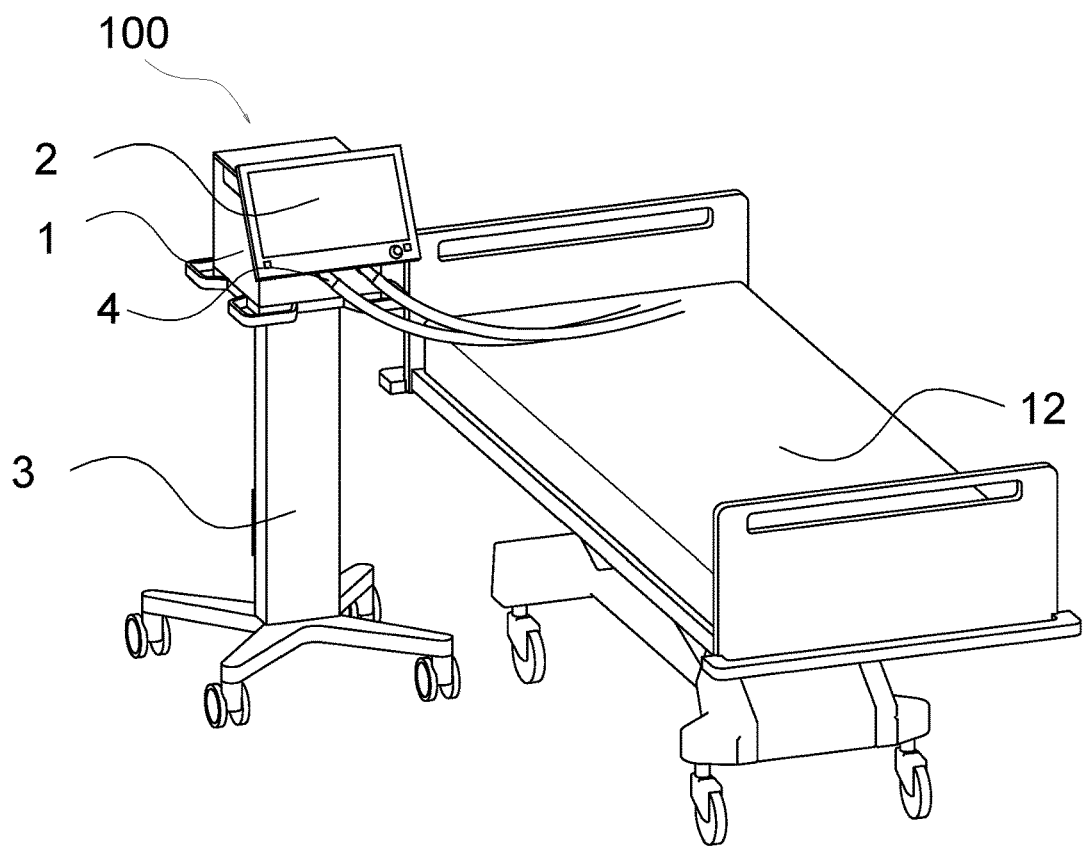

If the ventilator 100 also allows a configuration with patient connections 4 and operating part 2 in the same orientation as is shown in FIG. 4*c*, it is also possible to always leave the basic unit 1 in this position and to select the arrangement with respect to the hospital bed 12 such as it is shown in FIG. 6*e* and in FIG. 6*f*. Even though the lengths of the ventilation tubes 5 are not optimal in this case and the accessibility of the patient connections 4 is limited, the need to reconfigure the ventilator 100 is eliminated, which may be advantageous in some applications (frequent change of patients and frequent change between left and right positions with respect to the hospital bed 12). The patient connections 4 are advantageously configured in such an arrangement as rotatably angled grommets, which can be oriented at a certain angle towards the patient in order to make it possible to keep the necessary lengths of the ventilation tubes 5 as short as possible.

Figure 6G:
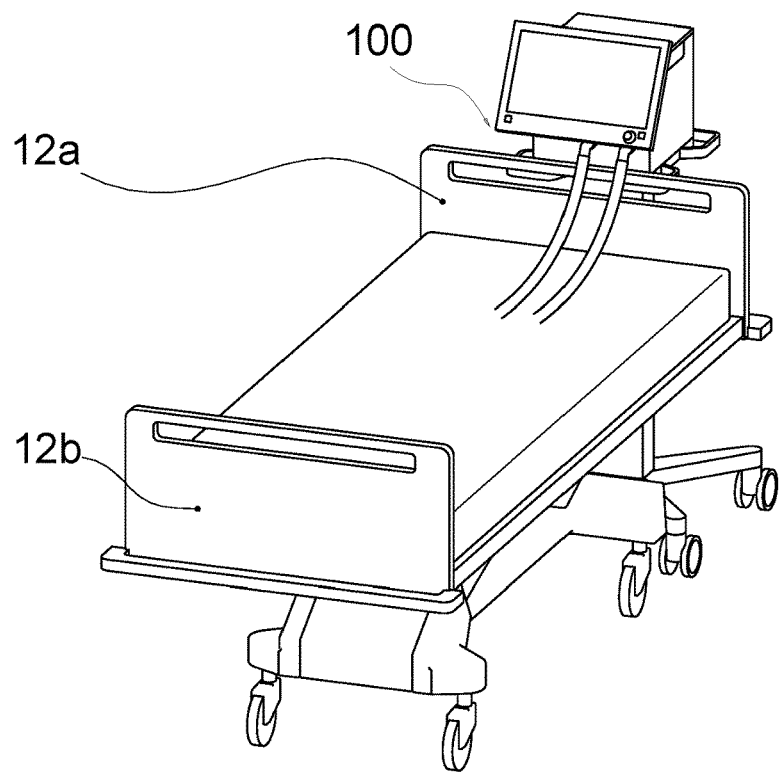
Figure 6H:
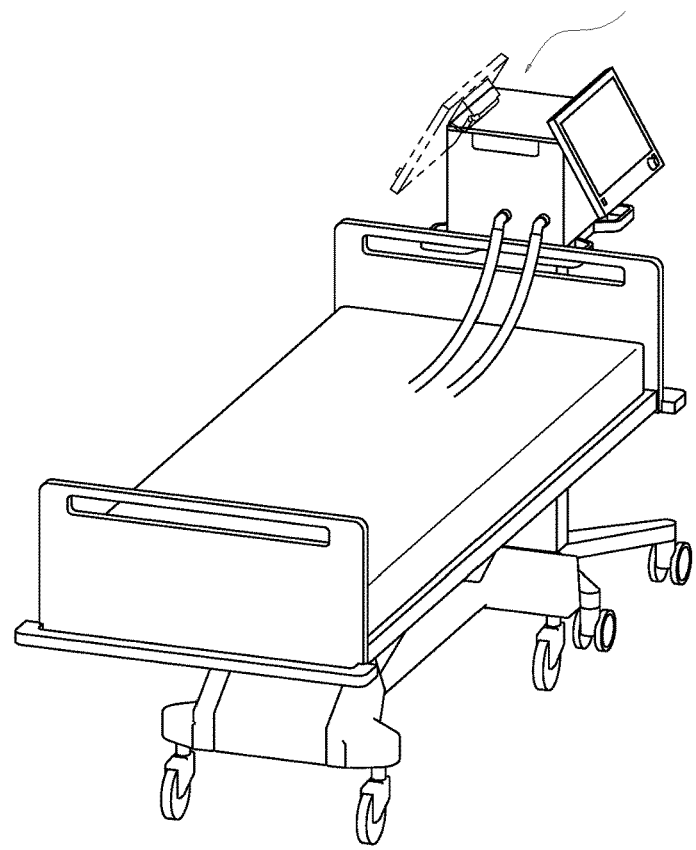

A device configuration according to FIG. 4*c* may also be advantageous for a position of the ventilator 100 behind a head end 12*a* of the hospital bed 12, because the ventilation tubes 5 are oriented towards the patient and the user interface 2 is oriented at the same time towards a foot end 12*b* of the hospital bed 12, where it can be readily seen by the physician, cf. FIG. 6*g*. If the physician then moves to the head of the patient, for example, in order to check the intubation, it may be advantageous if he can temporarily bring the user interface 2 into a position on the left or on the right of the patient connections 4, depending on which side of the hospital bed 12 he is standing, in order to be able to better read and operate them, as it is shown in FIG. 6*h*.

In order to make a complete configurability of the system comprising the basic unit 1 and the trolley 3 possible, which makes possible all the arrangements as shown in FIGS. 6*a-h* and thus allows maximum flexibility for the user in terms of setting up his workplace, the connection between the support plate 14 of the trolley 3 and the basic unit 1 preferably has a 90° rotation symmetry as well. For repositioning, the basic unit 1 is preferably unlocked again and, depending on the position, it is placed back on the trolley 3, rotated by 90° or 180°. As an alternative, a rotating device, with which the basic unit 1 can be turned on the trolley 3, which will, however, snap in at 90° increments in this case, may be provided for this exemplary embodiment as well.

In order to make the function shown in FIGS. 5*a-e* reliable and user-friendly, the rotating mechanism 9 preferably has at least one of the properties described below, which may also be combined with one another:

Firm seating of the cover plate 10 in the defined use positions, so that the user interface 2 is connected to the basic unit 1 with as little clearance as possible, blocking of the vertical rotary movement when the user interface 2 is in one of the use positions (FIG. 5*a*, FIG. 5*e*) in order to avoid incorrect operation, easy rotary movement during the rotation (FIG. 5*c*), noticeable snapping in when the use positions are reached, rotation stops at the end positions (FIG. 5*a*, FIG. 5*e*), so that the rotating mechanism 9 remains limited to a defined angle range, equaling 180° in the exemplary embodiment. A corresponding limitation to 360°, 540° or 720° may likewise be provided. An uncontrolled twisting of the cable 8 (system cable or a plurality of cables), which connects the basic unit 1 to the user interface 2, is avoided hereby, and there are no functional elements in the center of rotation, because this space is needed for passing through the cable 8 (system cable or a plurality of cables).

Two exemplary embodiments will be shown below, in which the aforementioned technical features are at least partially implemented. The exemplary embodiments pertain to a device with a square layout and three possible use positions of the user interface as in FIGS. 4*a-c*, but are, in principle, also applicable to a device with only two possible use positions according to FIGS. 5*a-e*.

Figure 7A:
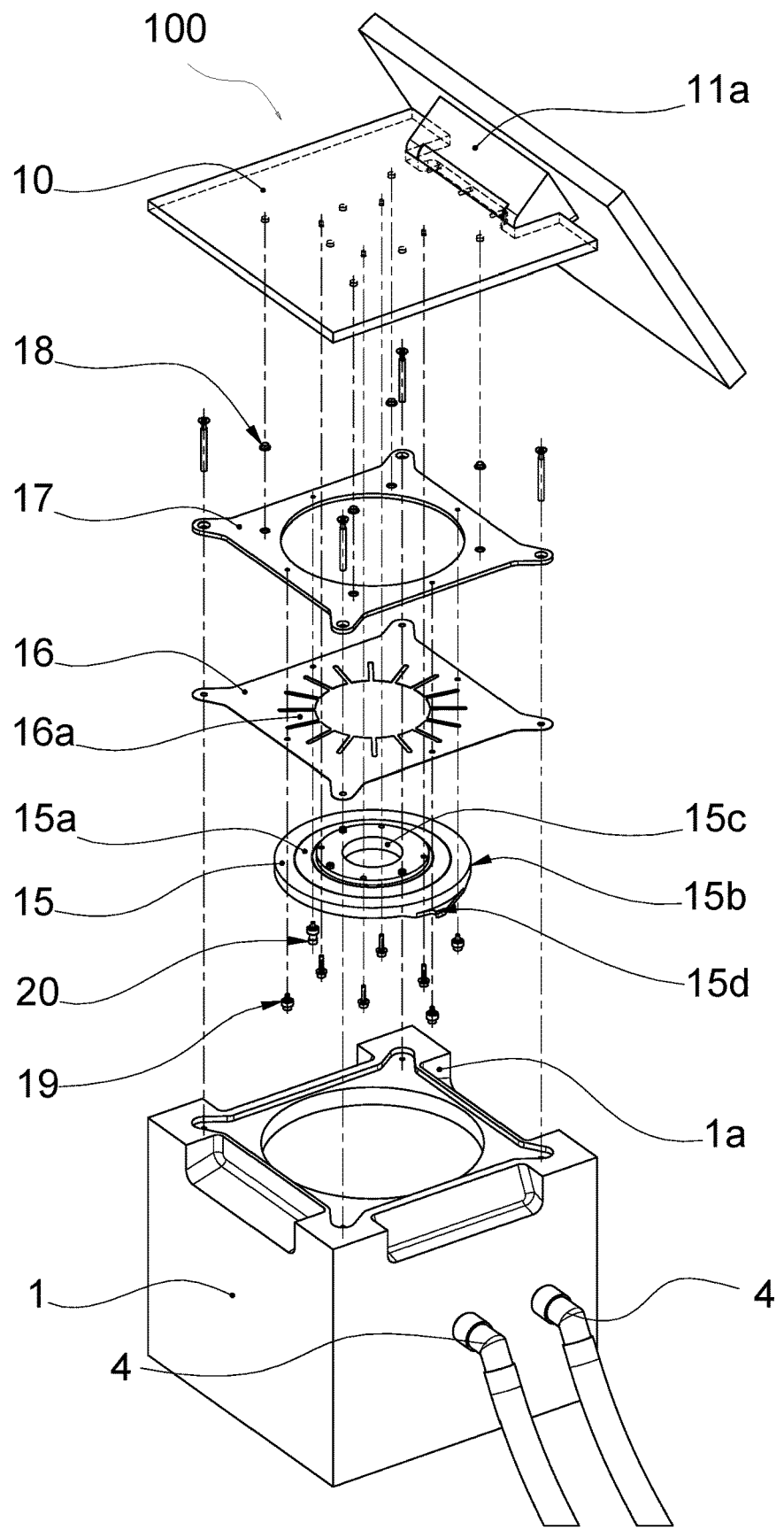
FIGS. 7a-7c are perspective views of a preferred embodiment of a rotating mechanism for a ventilator according to the present invention.
Figure 7B:
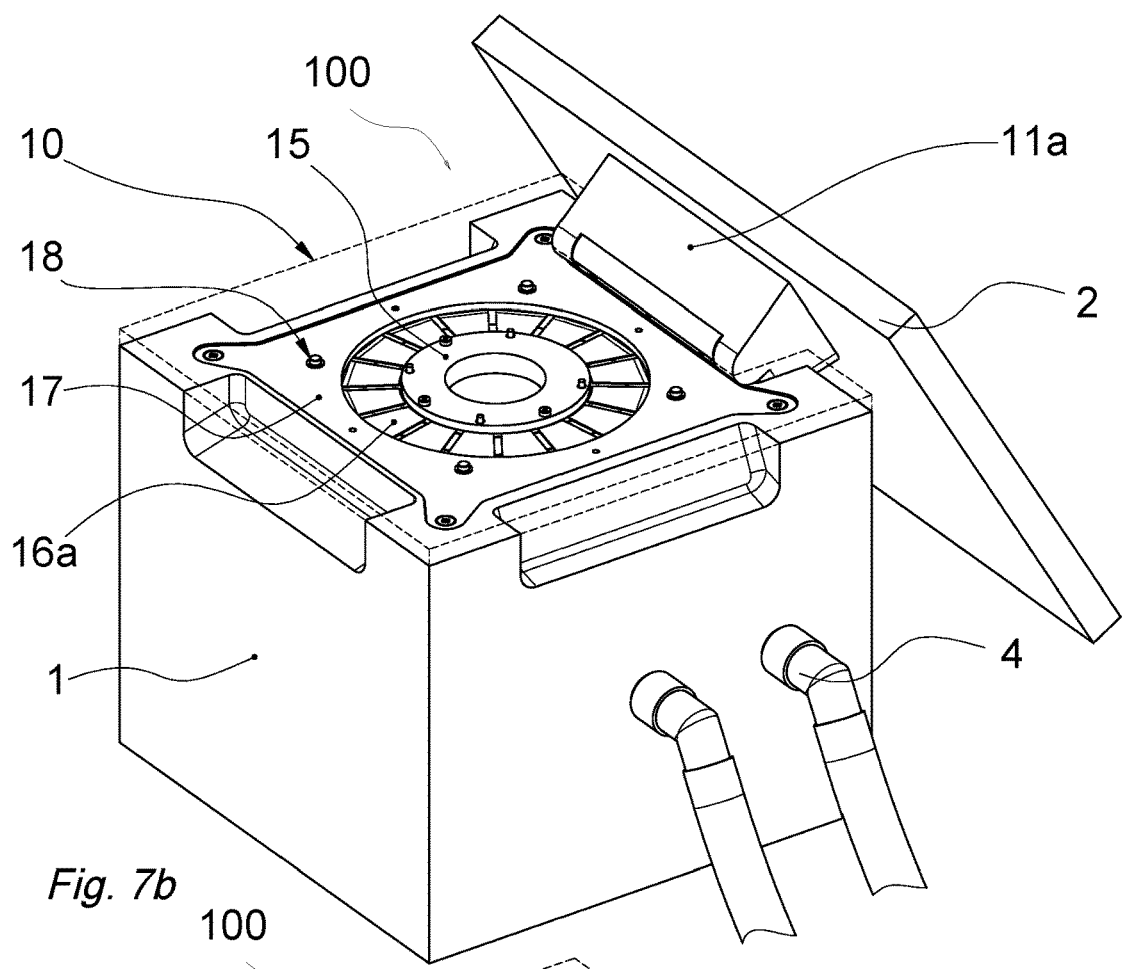
Figure 7C:
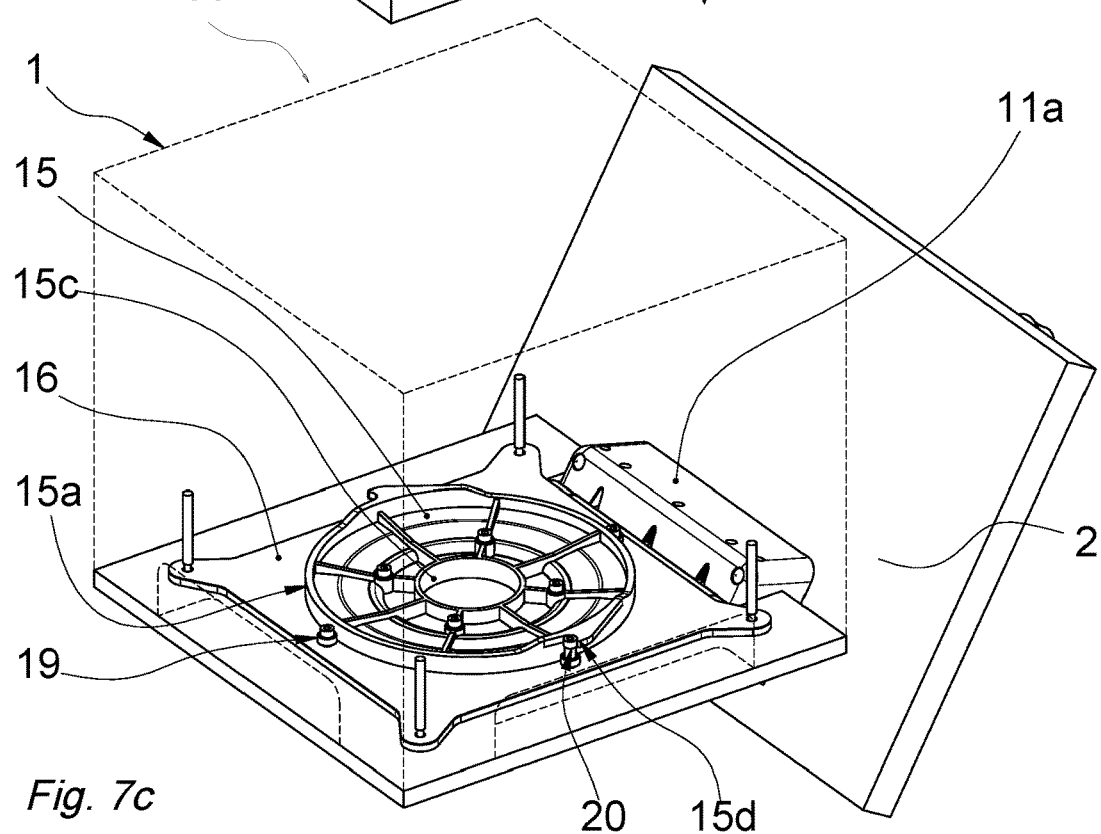

Exemplary Embodiment 1 (FIGS. 7*a-c*)

A sliding disk 15, especially one made of plastic, is rigidly connected to the cover plate 10, for example, by screw connection. In the mounted state, the sliding disk 15 and hence also the cover plate 10 are pressed down onto the basic unit 1 via a circularly arranged plurality of leaf springs 16*a*, which are combined into a spring steel sheet 16, which is in turn connected rigidly, for example, screwed to the basic unit 1 by means of a sheet-metal holder 17. The leaf springs 16*a* lie for this purpose on a flatly inclined conical surface 15*a* of the sliding disk 15 and also slide down on this during a rotary movement. To reduce the sliding friction, a life-time lubrication is preferably provided with grease.

Four locking nubs 18, which are recessed into the cover plate 10 and which are also configured as sliding feet at the same time, slide over the sheet-metal holder 17 until one of the 90° positions is reached, after which they drop, driven by the leaf springs 16*a*, into complementary screw holes in the sheet-metal holder 17 and thus form the desired locking function. This sliding function may also be improved by life-time lubrication. The leaf springs 16*a* still have a pretension in this position of the mechanism as well and act via a relatively large diameter, so that good support of the cover plate 10 with respect to the basic unit 1 is ensured. Due to this configuration of the locking function in interaction with the action of the leaf springs 16*a*, the cover plate 10 is lifted off from the basic unit 1 by a certain amount, for example, 1 mm, during the rotation, so that only the mounting elements provided for that purpose will be meshing, while grazing between the basic unit 1 and the cover plate 10 is prevented from occurring.

The radial mounting is brought about by means of four support rollers 19, which are configured as ball bearings and which are fastened on the sheet-metal holder 17 and roll on an outer cylindrical surface 15*b* of the sliding disk 15. A simple mounting by means of a central pin was not deliberately selected in order to leave space in the center of rotation for a passage 27 for passing through cables 8. A central opening 15*c* is provided for this purpose in the sliding disk 15.

A stop pin (positioning pin) 20, which is connected to one of the support rollers 19 and which is configured as a screw head, forms the desired end stops for the rotating mechanism 9 together with two stop bosses 15*d* formed in one piece on the sliding disk 15.

Figure 8A:
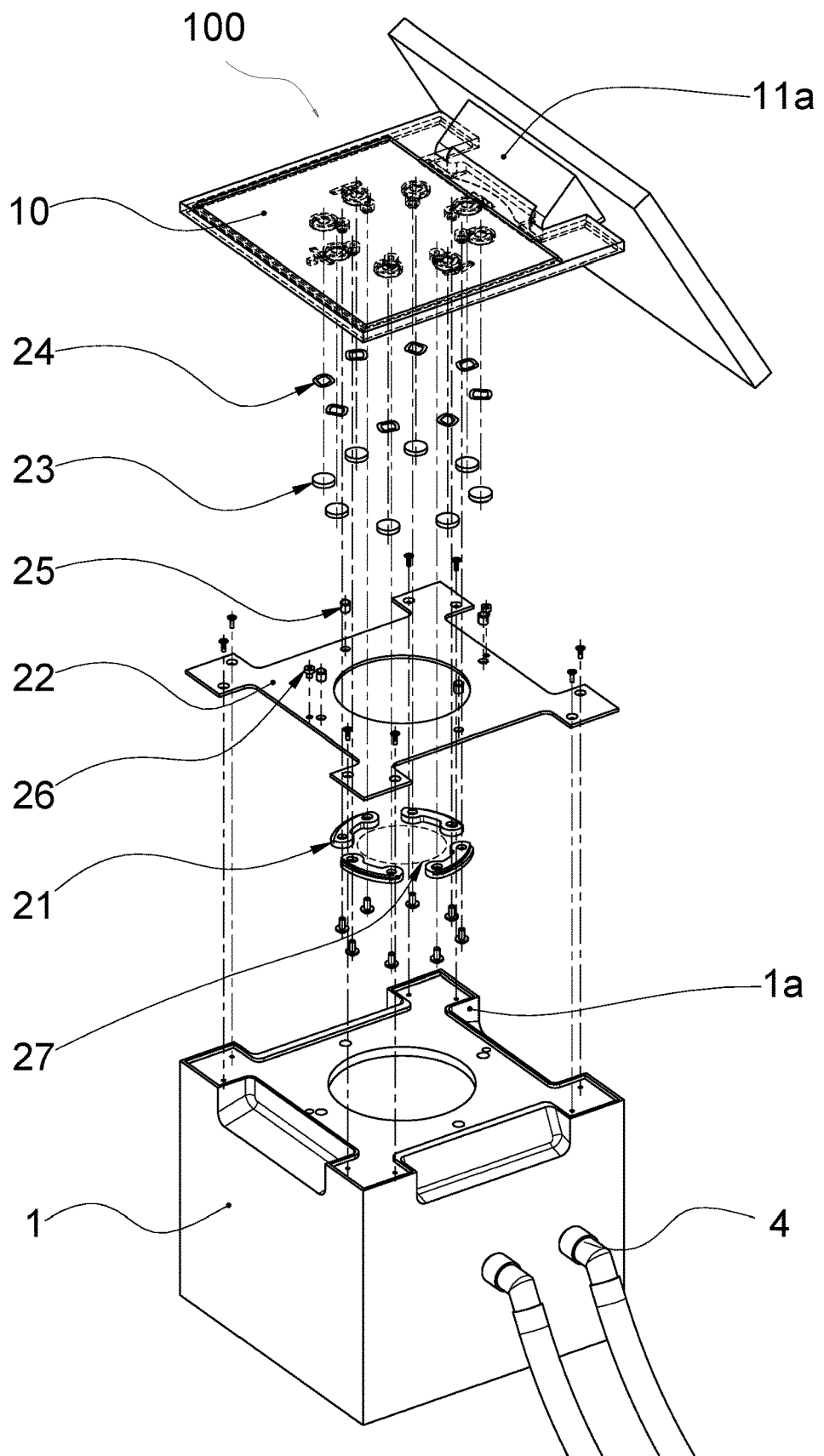
FIGS. 8a-8c are perspective views of another preferred embodiment of a rotating mechanism of a ventilator according to the present invention.
Figure 8B:
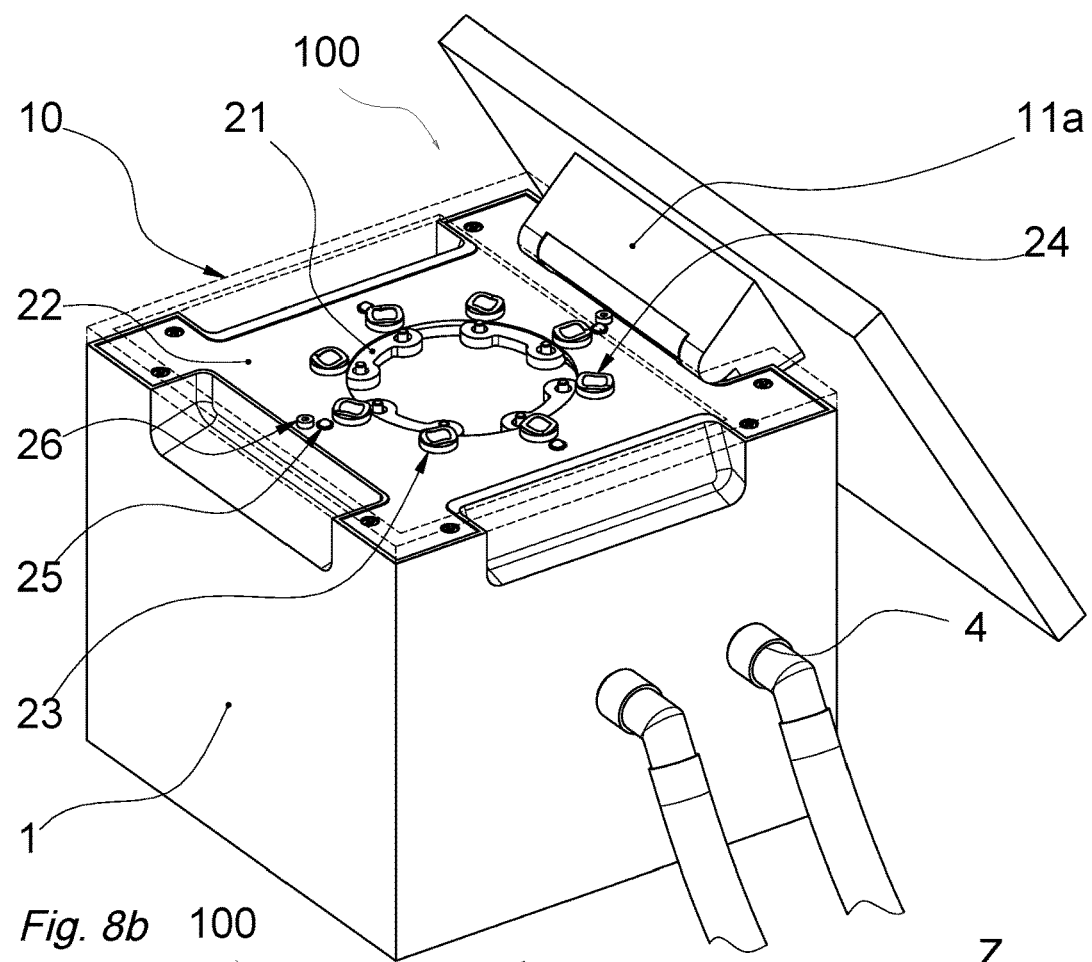
Figure 8C:
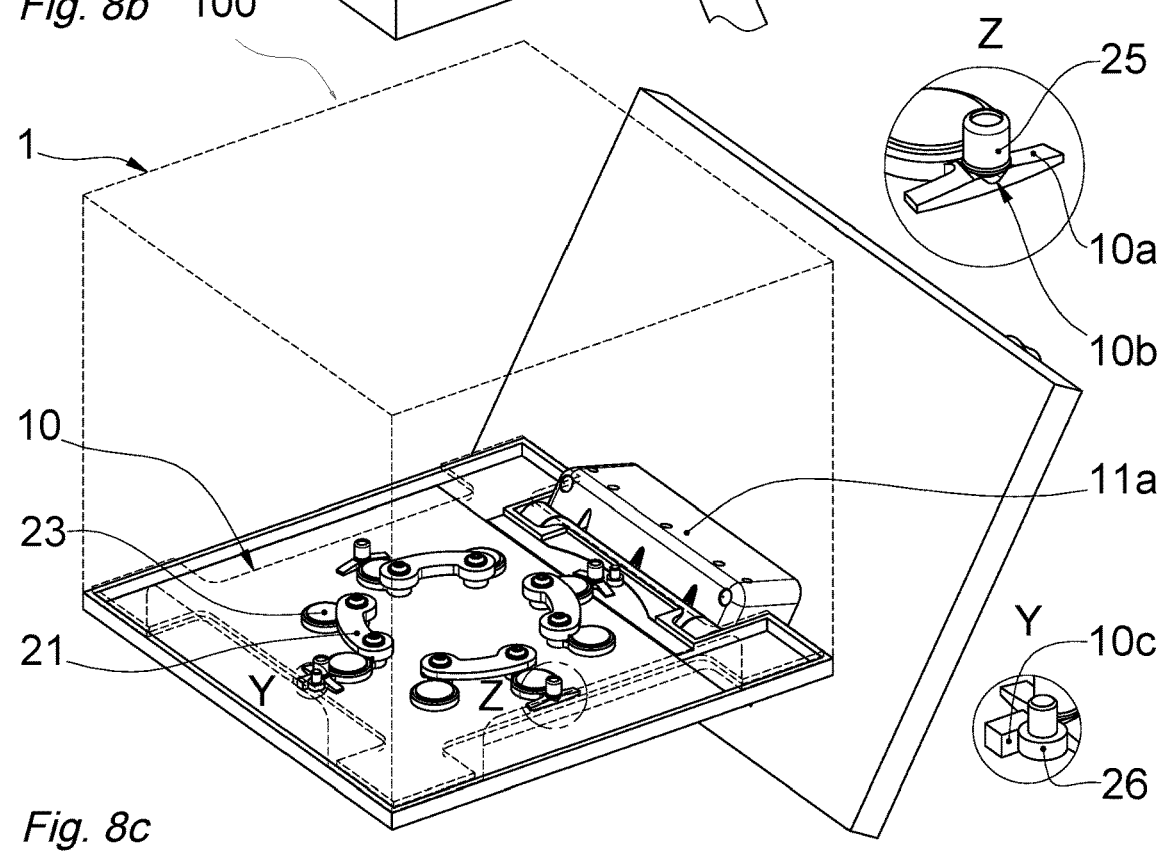

Exemplary Embodiment 2 (FIGS. 8*a-c*)

A slide bearing 21 acting both axially and radially, which is made of a slidable plastic, which is divided, for example, into four segments, in order to make it possible to set the external diameter tolerance more accurately than it would be possible with a one-part plastic ring, is connected rigidly, for example, screwed to the cover plate 10. The complementary axial and radial running surfaces are formed by a bracket 22, which is rigidly connected, for example, screwed to the basic unit 1.

To make clearance-free mounting possible in the axial direction, a circularly arranged plurality of sliding blocks 23 push the cover plate 10 off from the bracket 22 by means of spring washers 24, for example, corrugated washers, which are located above them.

Snapping in at 90° increments is brought about by two or four commercially available first ball catches 25, which are pushed in over ramps 10*a* recessed into the cover plate 10 shortly before the respective use position is reached and then snap into depressions 10*b* complementary to the balls of the first ball catches 25 when the use position is reached.

The end stops are formed in the exemplary embodiment by two screw heads 26, which are connected to the bracket 22 and which come into contact with a projection 10*c* formed in the cover plate 10 when the respective end position is reached. All running surfaces of the mechanism may be lubricated with a grease intended for the life of the product for smooth running. This mechanism also has a passage 27 for passing one or more cables 8, especially system cable, through the center of rotation, because a certain diameter is open here.

Blocking of the Vertical Rotary Movement (FIG. 7*a*, FIG. 8*a*)

The blocking of the rotary movement with the user interface 2 pivoted down is brought about in both of the above exemplary embodiments by the swivel joint housing 11*a* pivoting into a recessed grip 1*a* provided on the basic unit 1, so that a vertical rotary movement is prevented by positive locking. As an alternative or as a support for this, an inner mechanism may be embodied, which blocks the rotating mechanism 9 when the user interface 2 is pivoted down, for example, via a push rod entering the mechanism in the manner of a crank mechanism or in the manner of a detent pawl extending during pivoting down (no figures are available).

The swivel joint 11, which is suitable in a preferred manner for an operating element, for a monitor and/or for a display, preferably for a user interface 2 with touch function and with possible additional operating elements, and which makes possible, in addition, an approximately horizontal position of the user interface 2, as is shown in FIG. 5*b*, advantageously has at least one of the following structural features, which may, in turn, also be combined as needed:

Elimination of an unlocking element, which would have to be actuated in order to change the swivel angle (advantageous in respect to the operating convenience and hygiene)

Instead, a friction element, whose friction torque is high enough to support typical forces that the user applies to the operating part during the actuation of the touch function or of other operating elements to the extent that no accidental change in the setting of the swivel angle will occur.

A spring element for compensating the torque acting on the swivel joint 11 due to the weight of the user interface, so that the sum of the friction torque, weight and spring torque during the upward and downward pivoting are at least approximately equal.

Optionally a locking element, which brings about a stepwise adjustability of the swivel joint instead of a continuous adjustability, and/or by which the range of the swivel angles intended as a use position can be clearly distinguished haptically from the approximately horizontal position (FIG. 5b), which shall only be used to reconfigure the ventilator 100 according to FIGS. 5a-e.

The above properties are covered by the exemplary embodiment shown below. The exemplary embodiment pertains here to a basic unit 1 with a square layout and three possible use positions of the user interface 2 as in FIGS. 4a-c, but is also applicable, in principle, to a basic unit 1 with only two possible use positions according to FIGS. 5a-e.

Exemplary Embodiment (FIGS. 9a-d)

Figure 9A:
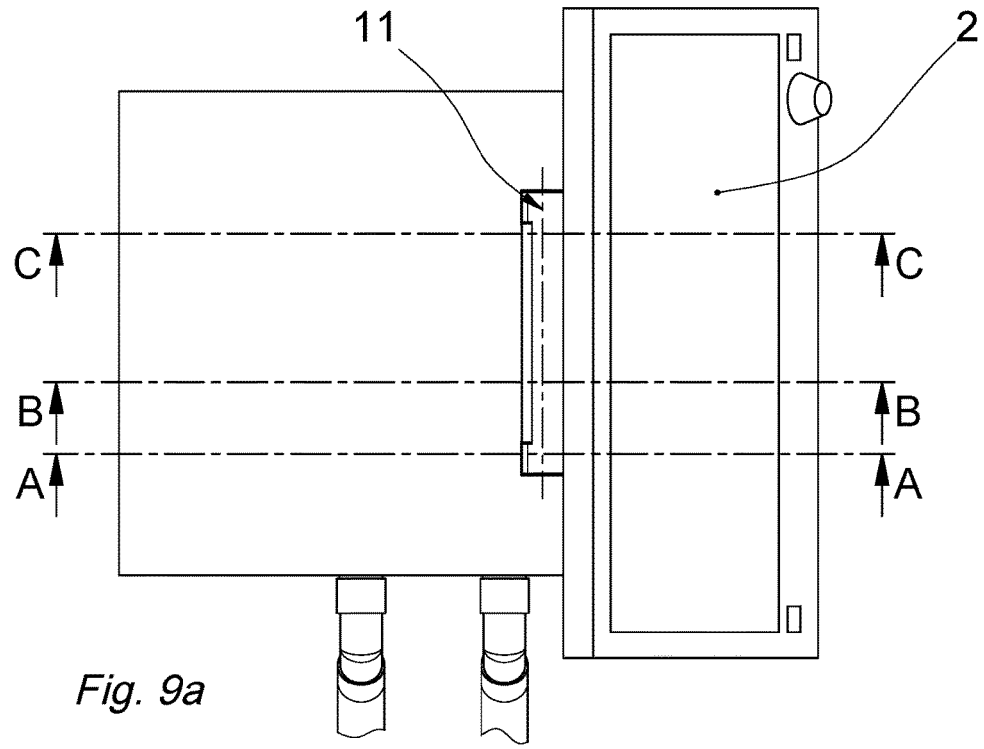
FIG. 9a is a top view of a preferred embodiment of a swivel joint for a ventilator according to the present invention.

An exemplary swivel joint 11 is shown in three section planes, which are defined in FIG. 9a. The section plane A-A (FIG. 9b) shows a friction element, two of which are present in the exemplary embodiment, comprising an axle piece 28 connected permanently to the cover plate 10 and preferably consisting of metal, and a bearing block 29, which is permanently connected to the user interface 2 and preferably consists of plastic, and whose bearing bore forms a press fit for the axle piece 28, which press fit can be set by means of a clamping bolt 30, in such a manner that the friction torque can be set by tightening or loosening the clamping bolt 30. A housing opening 11b in the swivel joint housing 11a makes adjustment possible in the mounted state as well.

The section plane B-B (FIG. 9c) shows a spring element, which is present as four spring elements in the exemplary embodiment, comprising a commercially available tension spring 31, which is hung with its upper end to a holding structure 32 connected to the axle piece 28 and hence to the cover plate 10 and with its lower end to an abutment 11c formed integrally in one piece with the swivel joint housing 11a. The swivel joint housing 11a is rigidly connected, in turn, to the user interface 2. Due to the action of the pretensioned tension springs 31, an approximately equally strong compensation of the weight of the user interface 2 is achieved at least in the angle range of the user interface 2 intended as the use position (for example, 0° to 45° against the vertical direction), because the effective lever length h about the pivot axis of the swivel joint 11 is increased by the selected arrangement during the upward pivoting of the user interface 2, while the pretensioning force of the tension spring 31 decreases at the same time.

The section plane C-C (FIG. 9d) shows a locking element, which is present as six locking elements in the exemplary embodiment, comprising a commercially available second ball catch 33, which is recessed into a sleeve 34, which is permanently connected, for example, screwed to the axle piece 28 and hence to the cover plate 10, and a slide block 35 with a plurality of first indentations 35a, which are complementary to the ball of the second ball catch 33 and which define the locking positions for the intended use positions (at 5° increments from 0° to 45° in the example).

Another indentation 35b fixes the user interface 2 in the approximately horizontal position according to FIG. 5b in order to make a reconfiguration of the ventilator 100 possible according to FIGS. 5a-e after setting this position. Since the ball of the second ball catch 33 is pressed in less far between the first indentations 35a than in the area 35c without first indentations 35a, the adjustment between the intended use positions runs noticeably more smoothly than the transition to the approximately horizontal position. As a result, the user can easily make a distinction haptically between the normal use positions and the special, approximately horizontal position, which must be assumed for the reconfiguration of the ventilator 100.

Possible Alternative Embodiments for a Friction Element

Instead of a friction pairing functioning with radial pressing, as in the above exemplary embodiment (FIG. 9b), one or more axially acting friction brakes according to the principle of action of a multiple-disk clutch or one or more conical friction pairings, which increase the frictional effect due to the wedge effect of the cone angle, are also conceivable, and a defined pressing force and a friction torque resulting therefrom could be generated in this case, for example, by means of one or more, correspondingly pretensioned compression springs or disk springs arranged concentrically to the axle piece 28.

Possible Alternative Embodiments for a Spring Element

Figures 9B, 9C, 9D:
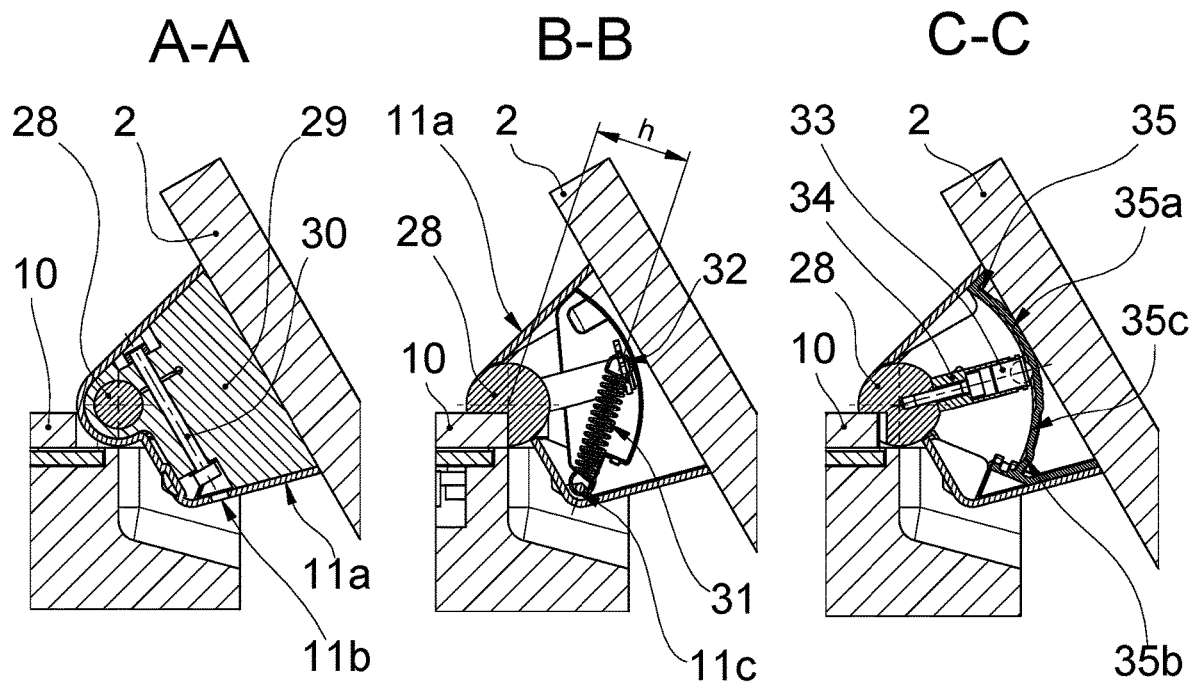
FIGS. 9b-9d are partial sectional views of the preferred embodiment of a swivel joint for a ventilator of FIG. 9a according to the present invention.

To compensate the torque that results from the weight of the user interface 2, it is also possible to use, instead of an arrangement of one or more tension springs 31, as they are shown in FIG. 9c, for example, one or more pretensioned leg springs or volute springs. The latter possess the special property of making available a constant torque over a broader range of angles, which is advantageous for the desired compensation compared to a spring whose torque decreases when the operating part is being pivoted up.

Possible Alternative Embodiments for a Locking Element

One or more second ball catches 33 may also be arranged in the axial direction instead of being arranged in the radial direction, as in the exemplary embodiment (FIG. 9d). Second ball catches 33 and complementary first indentations 35a are arranged now along an axis parallel to the central axis of the axle piece 28, and these axes are as far apart from one another as possible, so that the holding torque brought about by the locking function becomes as high as possible. An arrangement as shown in FIG. 9d may preferably also be provided, instead of with a second ball catch 33 having locking balls, with one or more cylindrical locking rods acted on by spring force, which have a greater length at right angles to the section plane of FIG. 9d. The complementary first indentations 35a and the additional indentation 35b, into which the locking rod or locking rods falls/fall, have a corresponding cylindrical groove shape in this case. The advantage of such a configuration would be the larger active surfaces compared to a spherical indentation and hence a reduced tendency to wear of the indentations.

Downward Limitation of the Swivel Angle of the User Interface

One peculiar feature of the exemplary embodiment for a ventilator 100 with a basic unit 1 with a square layout and three possible use positions of the user interface 2, as is shown in FIGS. 4a-c, is that in a configuration of the ventilator 100 with patient connections 4 in the same orientation as the user interface 2 (FIG. 4c), the user interface 2 can only be pivoted down up to a certain angle, for example, 25° against the vertical direction, because it would otherwise collide with the patient connections 4 and/or with the ventilation tubes 5, as it is shown in FIG. 10b. By contrast, the user interface 2 can be pivoted, as is shown in FIG. 10c, into an at least approximately vertical position in a configuration of the ventilator 100 with patient connections 4 laterally to the user interface 2 (FIG. 4a or FIG. 4b).

In order to make it possible to use the entire range of swivel angles of the user interface 2 in a device configuration according to FIG. 4a or FIG. 4b, but to limit it at the same time in a configuration according to FIG. 4c such that a collision with the patient connections 4 is avoided, the recessed grips 1a molded in the basic unit 1 have different configurations: The recessed grip 1a, which is oriented towards the patient connections 4, has an angulated stop face 1b for the swivel joint housing 11a, by which the pivoting down of the user interface 2 is limited such that a collision with the patient connections 4 will be avoided. The recessed grips 1a that are located laterally with respect to the patient connections 4 have, by contrast, at least approximately vertical stop faces 1c, which make it possible for the user interface 2 to be able to be pivoted down into an at least approximately vertical position.

The aforementioned exemplary embodiments for rotating mechanisms and swivel joints do not represent a limitation of the general inventive idea. It is conceivable in this respect, in particular, to combine the different technical features with one another, so that not only especially suitable swivel joints and rotating mechanisms, but also corresponding combinations of rotating mechanisms and swivel joints may be made available and can be summarized under the present invention.

A rear side of a ventilator 100 typically has rather minor decorative and also hygienic requirements, so that it can preferably be used for the placement of at least one interface and preferably of a plurality of or all interfaces for cables 8 and tubes, which are installed permanently, for example, gas inlet tubes, power cords, network cables, and for other functional elements such as main switches, ventilation inlets or battery racks.

Figure 11A:
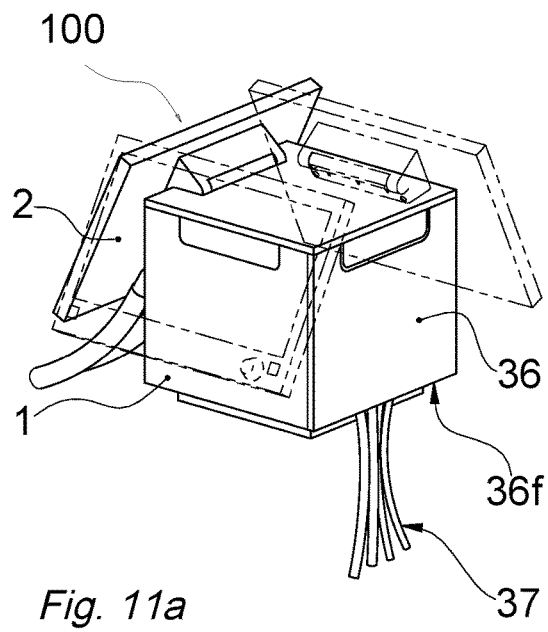
FIG. 11a-11d are perspective views of a preferred embodiment of a ventilator according to the present invention with hidden device connections.
Figure 11B:
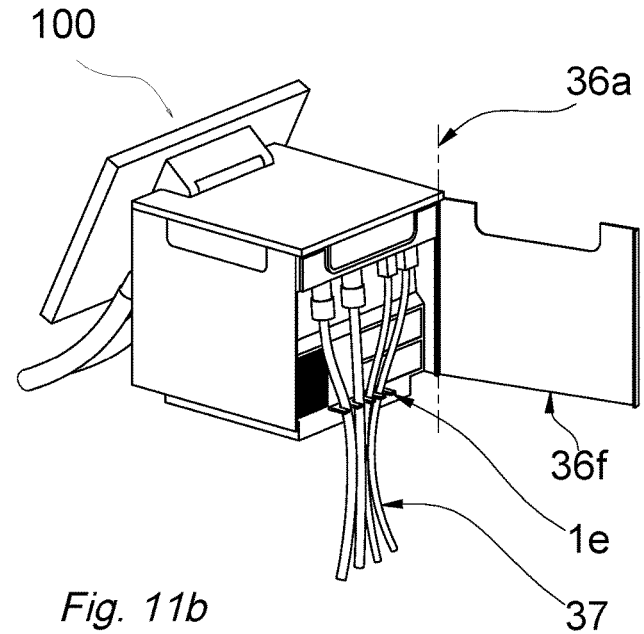
Figure 11C:
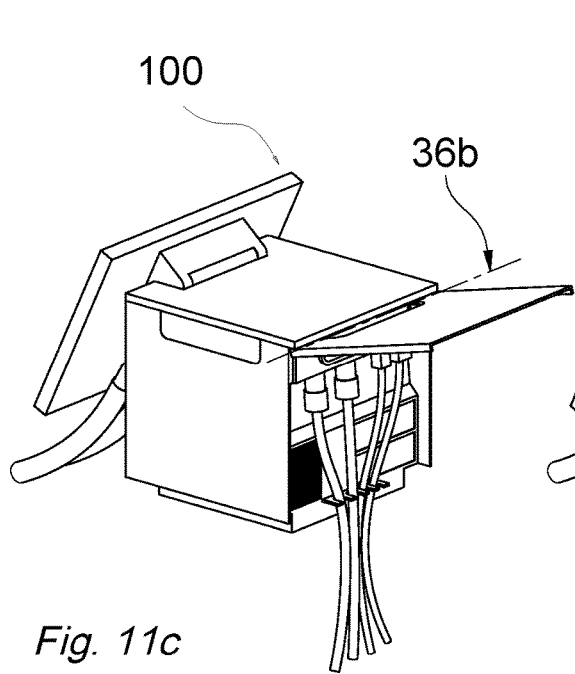
Figure 11D:
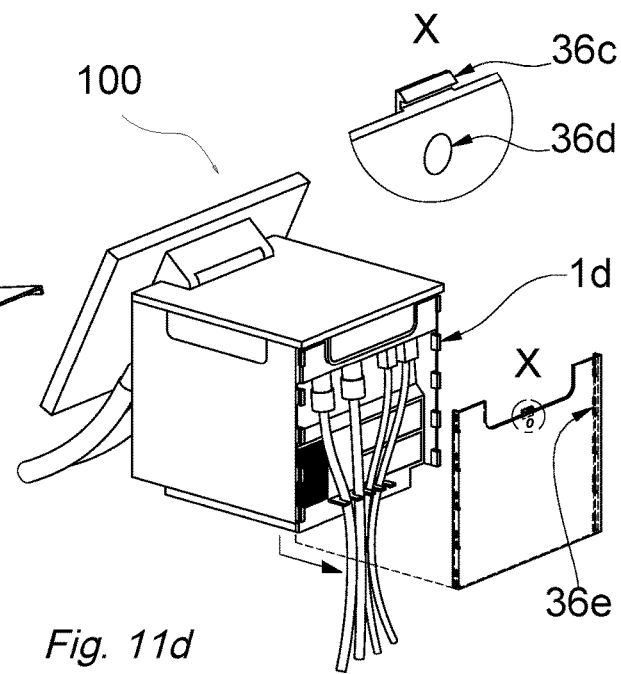
Figure 12:
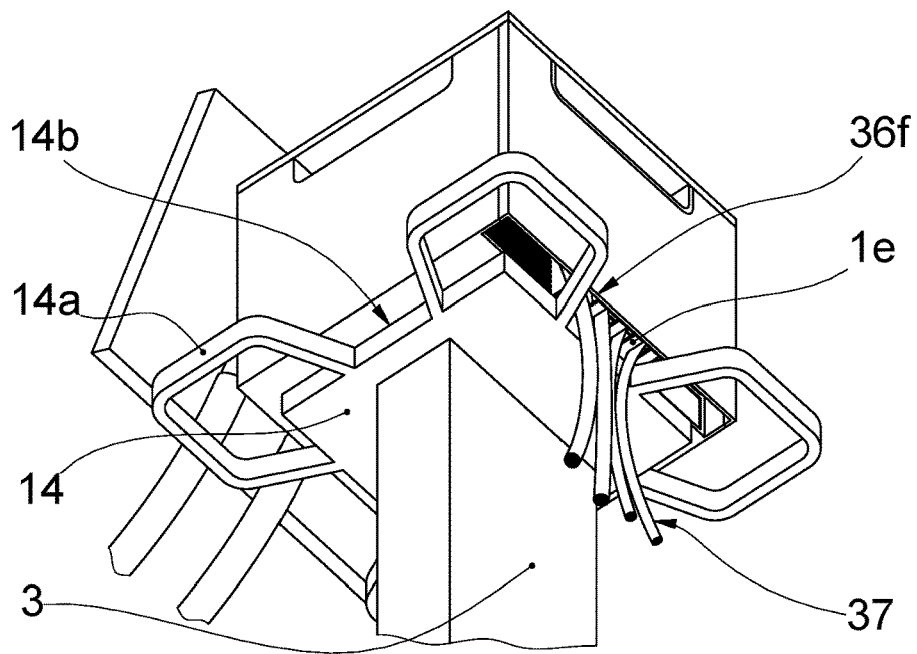
FIG. 12 is a perspective view of a preferred embodiment of a ventilator according to the present invention with hidden device connections on a trolley.
Figure 13A:
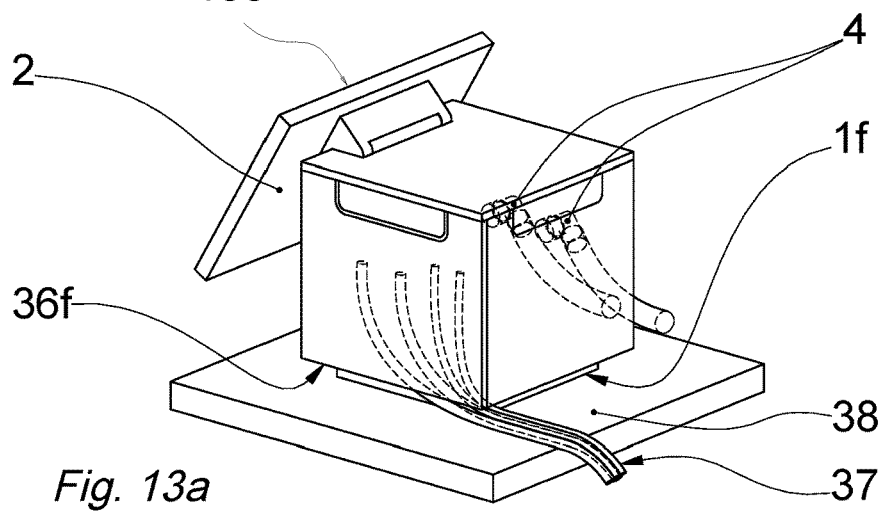
FIGS. 13a-13b are perspective views of a preferred embodiment of a ventilator according to the present invention with hidden device connections on a table leaf.
Figure 13B:
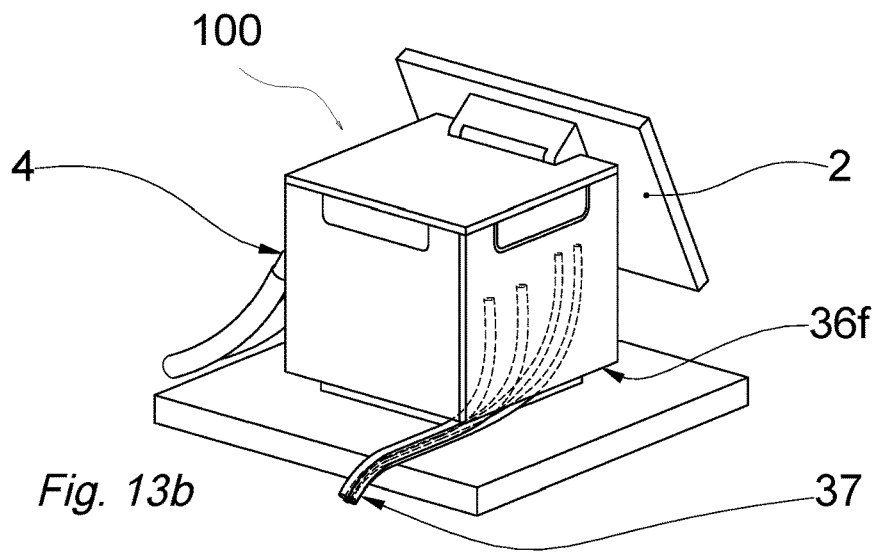

In a special embodiment, the ventilator 100 according to the present invention, which can be reconfigured according to FIGS. 4a-c or FIGS. 5a-e, is characterized in that the basic unit 1 has no such rear side in the sense that it is always the side facing away from the user. Therefore, such a ventilator 100 may advantageously have a design cover 36 closing the shape of the basic unit 1, which forms the left side or the right side of the device or the rear side depending on the configuration of the device in respect to the user interface 2. Such a design cover 36 is shown, for example, in FIG. 11a. The design cover 36 must be able to be opened or removed easily by the user in order to make the above-described cable and tube interfaces and other functional elements accessible. The design cover 36 may be configured for this purpose, for example, as a door with a vertical axis, as is shown in FIG. 11b, or with a horizontal axis 36b arranged in the vicinity of the top edge, or it may be detachable, e.g., by unlocking a locking element 36c and pushing down and hence moving out of a positive locking formed, for example, by tongue and groove elements 1d formed in sections. Cables and tubes 37 are led out and air is sucked in for cooling the device or also for a ventilation blower advantageously through an opening at the lower edge 36g of the design cover 36, so that no other openings are visible. This opening may have comb-like elements 1e in order to define the routing of the cables 8 and tubes. In the composite system with a trolley 3, the cables 8 and tubes can thus be led away, as is shown in FIG. 12a, downward essentially independently from a particular placement of the basic unit 1 on the trolley. Grips 14a, which may also be configured as rails with a standard section for placing accessories, for example, an articulated arm, are arranged on all sides at the support plate 14 in this exemplary embodiment. In addition, the support plate 14 preferably has central recesses 14b on at least three sides, so that the cables and tubes 37 can be led downward without collision, regardless of whether the patient connections 4 are positioned at the basic unit 1 in the forward direction, to the left or to the right relative to the trolley 3 (cf. FIGS. 6c-f).

One peculiar feature is, by contrast, the use of the ventilator 100 according to the present invention as a desk-top device: The lower edge 36f of the design cover 36 is located at such a spaced location from a table leaf 38 in this case by means of a base if made in one piece with the basic unit 1 that all cables and tubes 37 can be led out laterally—relative to the cover—to the left or to the right, without being excessively kinked. As a result, the two device configurations with the patient connections 4 arranged on the left-hand side (cf. FIG. 12b) and on the right-hand side (cf. FIG. 12c) with respect to the user interface 2 may also be used as a desk-top device because the cables and tubes 37 can be led away to the rear with respect to the user interface 2 in both configurations.

Simpler device variants can be derived from the ventilator 100 according to the present invention according to FIGS. 4a-c or FIGS. 5a-e by using the basic unit 1 described as a common basis, while the rotatable and pivotable functional assembly unit described, comprising the cover plate 10, the swivel joint 11 and the user interface 2, is replaced by a simplified, for example, non-movable or only pivotable operating module.

Figure 14A:
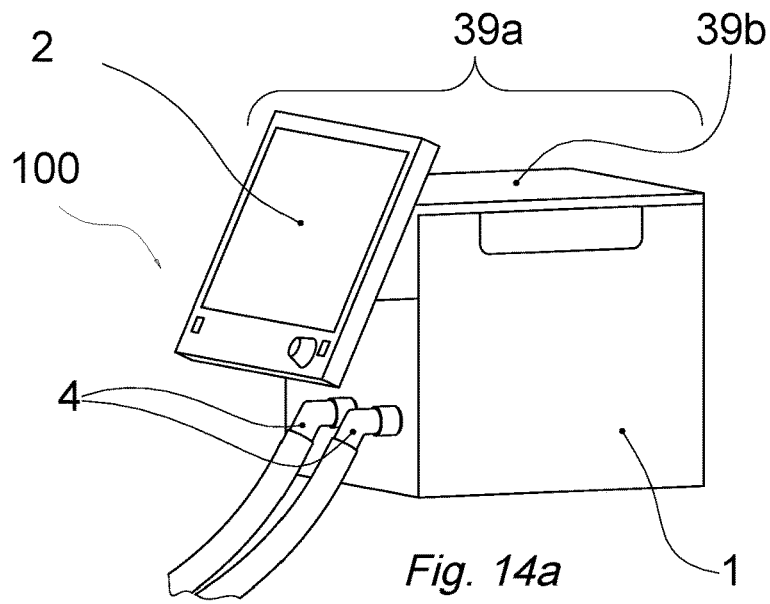
FIGS. 14a-14c are perspective views of another possible embodiment of a ventilator according to the present invention with stationary user interface.
Figure 14B:
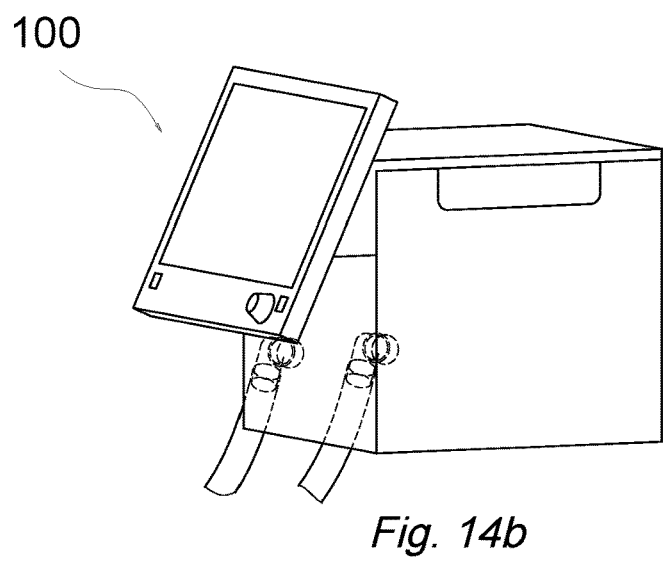
Figure 14C:
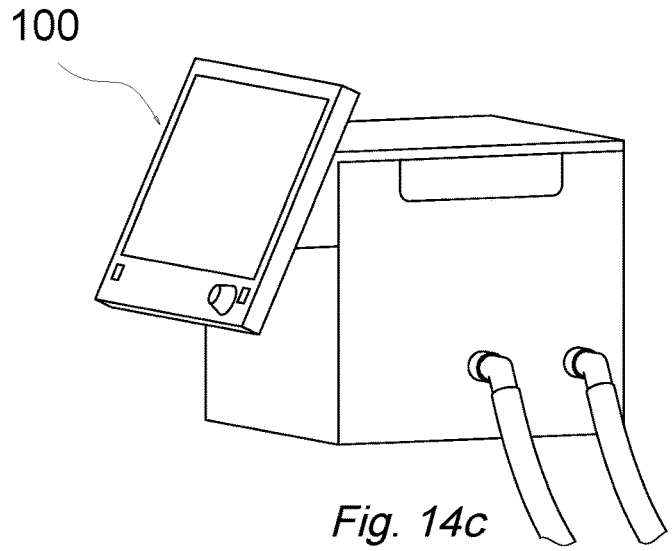

FIG. 14a shows a simplified ventilator 100 with a smaller user interface 2, which is arranged above the patient connections 4 and forms an operating module 39a together with a cover plate 39b connected permanently to this user interface. The cover plate 39b is connected permanently to the basic unit 1 in this exemplary embodiment. This device variant corresponds, in principle, to a compact ventilator 100 according to FIG. 2. If the basic unit 1 has a 90° rotationally symmetrical layout, as is shown in FIG. 4a-c, the operating module 39a may, instead, be permanently connected to the basic unit 1 in a position shifted by 90° to the right (cf. FIG. 14b) or to the left (cf. FIG. 14c), so that the user can choose between a ventilator 100 with patient connections 4 pointing forward, to the left or to the right depending on the preferred application (cf. FIGS. 6c-f). The configuration may be carried out in the factory or, for example, by a service technician at the location of the user.

Figure 15A:
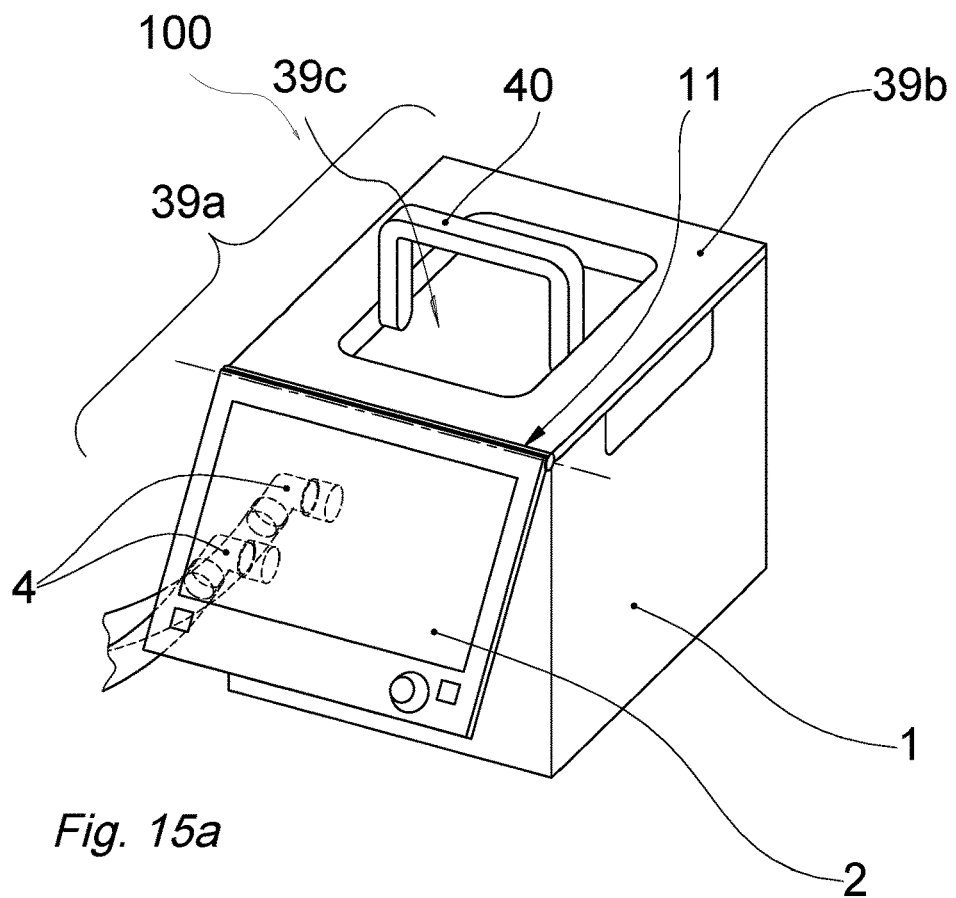
FIGS. 15a-15b are perspective views of another possible embodiment of a ventilator according to the present invention with a pivotable user interface of small dimensions.

FIG. 15a shows an especially compact ventilator 100, whose operating module 39a has an even smaller user interface 2, which is arranged laterally with respect to the patient connections 4 such that this does not top the top side of the cover plate 39b. The user interface 2 preferably has the same width as the basic unit 1, which emphasizes the compactness of the ventilator 100. A swivel joint 11 is preferably arranged between the user interface 2 and the cover plate 39b, so that the angle of the user interface 2 can be set to an advantageous position for the user. A carrying handle 40 for carrying the ventilator 100 may be arranged on the cover plate 39b. The carrying handle 40 can preferably be pivoted or tilted out about a horizontal axis and preferably held at the cover plate 39b such that this carrying handle is recessed in a recess 39c of the cover plate 39b in a folded-in state. A pivotable carrying handle 40 has the advantage that it influences the overall height of the ventilator 100 only slightly at best in the retracted state. As an alternative, the carrying handle 40 may also be arranged permanently at the cover plate 39b. The portability of the ventilator 100 is improved by means of a carrying handle 40.

Figure 15B:
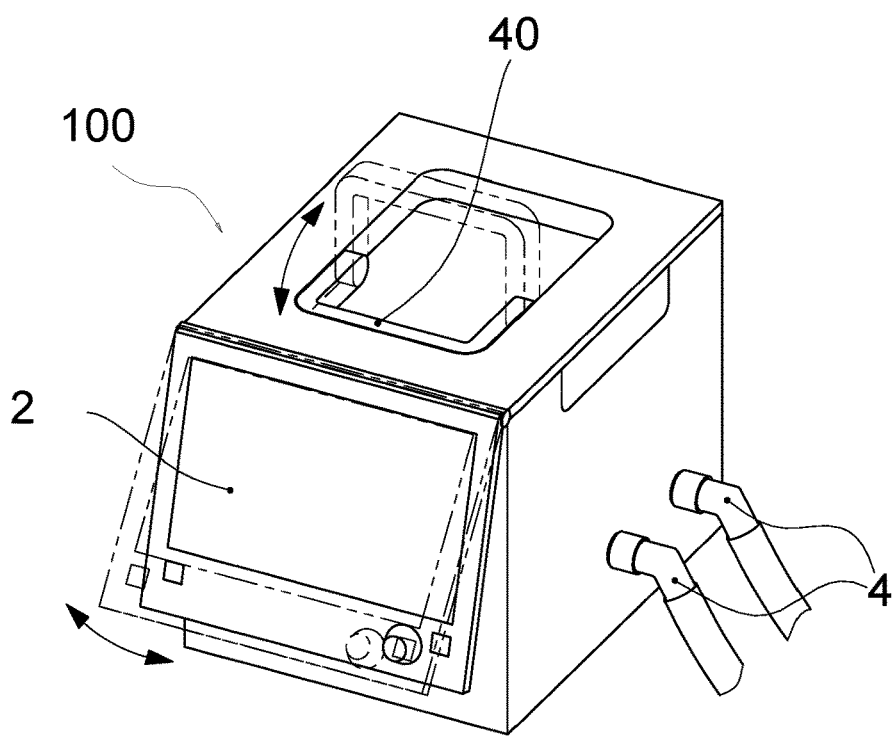

If the basic unit 1 has at least a layout that is rotationally symmetrically by 180°, as it is shown in FIGS. 5a-e, the operating module 39a, which has the user interface 2 and the cover plate 39b, may also be connected permanently to the basic unit in a position offset by 180°, as is shown in FIG. 15b, instead of as shown in FIG. 15a, so that the user has a choice between a ventilator 100 with patient connections 4 to the left or to the right depending on the preferred application (cf. FIGS. 6c, d). The configuration may also be carried out at the factory or, for example, by a service technician at the location of the user in the case of this device variant as well.

While specific embodiments of the invention have been shown and described in detail to illustrate the application of the principles of the invention, it will be understood that the invention may be embodied otherwise without departing from such principles.

The invention claimed is:

1. A ventilator comprising:
   a basic unit having side walls defining a layout of the basic unit and having a vertical axis;
   a cover plate configured with a shape that corresponds to a shape of the layout of the basic unit to form a covering surface at the basic unit;
   patient connections arranged at the basic unit; and
   a user interface arranged at the cover plate, wherein the cover plate is arrangeable at the basic unit at different angles with respect to the vertical axis, wherein the user interface is held at the cover plate pivotably about a horizontal pivot axis by means of a swivel joint, wherein the user interface is configured to be pivoted into a blocking position by means of the swivel joint with the cover plate in a use position, wherein a relative rotation of the cover plate with respect to the basic unit is blocked in the blocking position, and wherein the user interface can be pivoted into a releasing position, in which the relative rotation of the cover plate with respect to the basic unit is released from the use position.

2. A ventilator in accordance with claim 1, further comprising a rotating mechanism connected to the basic unit, wherein the cover plate is rotatably held at the basic unit about the vertical axis by means of the rotating mechanism.

3. A ventilator in accordance with claim 2, further comprising a locking mechanism, which impedes the relative rotation of the cover plate with respect to the basic unit at predefined distances.

4. A ventilator in accordance with claim 2, further comprising rotation stop elements to limit a rotation of the cover plate about the vertical axis with respect to the basic unit.

5. A ventilator in accordance with claim 1, wherein the cover plate has a layout configured rotationally symmetrical by 180° or by 90°.

6. A ventilator in accordance with claim 1, further comprising a locking device for holding the user interface in the blocking position relative to the cover plate.

7. A ventilator in accordance with claim 1, wherein the swivel joint is configured to pivot the user interface into an at least approximately horizontal position.

8. A ventilator in accordance with claim 1, wherein the swivel joint is configured to block the cover plate in the blocking position of the user interface with the cover plate in the use position.

9. A ventilator in accordance with claim 1, further comprising a trolley, wherein the basic unit is arranged on the trolley.

10. A ventilator in accordance with claim 9, wherein the trolley includes a support plate and the basic unit is detachably held at the trolley via the support plate.

11. A ventilator in accordance with claim 10, wherein the basic unit and the support plate are configured such that the basic unit can be arranged as well as fixed in two positions differing from one another by 180° or in at least three positions differing from one another by 90°.

12. A ventilator in accordance with claim 1, the user interface is arranged linearly slidable at the cover plate.

13. A ventilator in accordance with claim 2, wherein the rotating mechanism has a central passage, through which cables can be passed or are passed for electrically coupling the user interface with the basic unit.

14. A ventilator in accordance with claim 1, wherein the basic unit comprises an opening with a cover and all device connections are accommodated behind the cover, which the cover does not exceed an outline layout of the basic unit or does so only insignificantly exceeds the outline of the basic unit.

15. A ventilator comprising:
    a ventilator basic unit having side walls defining a layout of the ventilator basic unit and having a vertical axis;
    a cover plate configured with a shape that corresponds to a shape of the layout of the ventilator basic unit to form a covering surface at the ventilator basic unit;
    ventilator patient connections connected to the ventilator basic unit;
    a user interface connected to the cover plate;
    a cover plate to ventilator basic unit connection configured to provide a moveable connection between the cover plate and the ventilator basic unit to arrange the cover plate, connected to the ventilator basic unit, with the cover plate shape that corresponds to a shape of the layout flush with the side walls of ventilator basic unit and to arrange the cover plate, connected to the ventilator basic unit, at different angles to the ventilator basic unit with respect to the vertical axis wherein the cover plate to ventilator basic unit connection comprises a rotating mechanism connected to the ventilator basic unit and connected to the cover plate, wherein the cover plate is rotatably held at the ventilator basic unit about the vertical axis by means of the rotating mechanism; and
    a swivel joint providing the connection of the user interface to the cover plate, whereby the user interface is pivotably connected to the cover plate for movement about a horizontal pivot axis, wherein the user interface is configured to be pivoted into a blocking position by means of the swivel joint with the cover plate is in a cover plate use position, wherein a relative rotation of the cover plate with respect to the ventilator basic unit is blocked with the user interface in the blocking position.

16. A ventilator in accordance with claim 15, further comprising rotation stop elements to limit a rotation of the cover plate about the vertical axis with respect to the ventilator basic unit.

17. A ventilator comprising:
- a ventilator basic unit having side walls defining a layout of the ventilator basic unit and having a vertical axis;
- a cover plate configured to form a covering surface at the ventilator basic unit;
- patient connections arranged at the ventilator basic unit;
- a swivel joint;
- a user interface connected to the cover plate by the swivel joint; and
- a cover plate to ventilator basic unit connection configured to provide a moveable connection between the cover plate and the ventilator basic unit to arrange the cover plate, connected to the ventilator basic unit, with the cover plate shape that corresponds to a shape of the layout flush with the side walls of ventilator basic unit and to arrange the cover plate, connected to the ventilator basic unit, at different angles to the ventilator basic unit with respect to the vertical axis,
- wherein the swivel joint connects the user interface to the cover plate pivotably about a horizontal pivot and the user interface is configured to be pivoted into a blocking position by means of the swivel joint, with the cover plate is in a use position, wherein a relative rotation of the cover plate with respect to the ventilator basic unit is blocked in the blocking position of the user interface.

18. A ventilator in accordance with claim 17, wherein the user interface blocking position is set with the user interface pivoted in an operating position with an operating position pivoting range between a vertical orientation of the user interface and a transition orientation of the user interface and wherein the releasing position has a releasing position pivoting range between the transition orientation of the user interface and a horizontal orientation of the user interface.

19. A ventilator in accordance with claim 1, wherein the user interface blocking position is set with the user interface pivoted in an operating position with an operating position pivoting range between a vertical orientation of the user interface and a transition orientation of the user interface and wherein the releasing position has a releasing position pivoting range between the transition orientation of the user interface and a horizontal orientation of the user interface.

20. A ventilator in accordance with claim 15, wherein the user interface blocking position is set with the user interface pivoted in an operating position with an operating position pivoting range between a vertical orientation of the user interface and a transition orientation of the user interface and wherein the releasing position has a releasing position pivoting range between the transition orientation of the user interface and a horizontal orientation of the user interface.

* * * * *